US009050267B2

(12) United States Patent
Weers et al.

(10) Patent No.: US 9,050,267 B2
(45) Date of Patent: Jun. 9, 2015

(54) DRY POWDER FORMULATIONS OF PARTICLES THAT CONTAIN TWO OR MORE ACTIVE INGREDIENTS FOR TREATING OBSTRUCTIVE OR INFLAMMATORY AIRWAYS DISEASES

(75) Inventors: Jeffry G. Weers, Belmont, CA (US); Nagaraja Rao, San Leandro, CA (US); Daniel Huang, Palo Alto, CA (US); Danforth Miller, San Carlos, CA (US); Thomas E. Tarara, Burlingame, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/982,630

(22) PCT Filed: Feb. 3, 2012

(86) PCT No.: PCT/US2012/023727
§ 371 (c)(1),
(2), (4) Date: Aug. 21, 2013

(87) PCT Pub. No.: WO2012/106575
PCT Pub. Date: Aug. 9, 2012

(65) Prior Publication Data
US 2013/0319411 A1 Dec. 5, 2013

Related U.S. Application Data

(60) Provisional application No. 61/439,527, filed on Feb. 4, 2011.

(51) Int. Cl.
| *A61K 9/14* | (2006.01) |
| *A61K 9/50* | (2006.01) |
| *A61K 9/00* | (2006.01) |
| *A61K 45/06* | (2006.01) |
| *A61K 31/40* | (2006.01) |
| *A61K 31/4704* | (2006.01) |
| *A61K 31/56* | (2006.01) |
| *A61K 31/58* | (2006.01) |
| *A61M 15/00* | (2006.01) |
| *A61K 9/16* | (2006.01) |

(52) U.S. Cl.
CPC ............... *A61K 9/50* (2013.01); *A61K 9/0075* (2013.01); *A61K 9/1611* (2013.01); *A61K 9/1617* (2013.01); *A61K 9/1623* (2013.01); *A61K 9/501* (2013.01); *A61K 9/5015* (2013.01); *A61K 45/06* (2013.01); *A61K 31/40* (2013.01); *A61K 31/4704* (2013.01); *A61K 31/56* (2013.01); *A61K 31/58* (2013.01); *A61M 15/00* (2013.01)

(58) Field of Classification Search
CPC ...... A61K 9/0073; A61K 9/0075; A61K 9/14
USPC ........................................................ 424/489
See application file for complete search history.

(56) References Cited

U.S. PATENT DOCUMENTS

| 736,102 A | 8/1903 | Howe |
| 6,309,623 B1 | 10/2001 | Weers et al. |
| 6,565,885 B1 | 5/2003 | Tarara et al. |
| 6,638,495 B2 | 10/2003 | Weers et al. |
| 7,172,752 B2 | 2/2007 | Watanabe et al. |
| 7,306,787 B2 | 12/2007 | Tarara et al. |
| 7,326,691 B2 | 2/2008 | Duddu et al. |
| 7,442,388 B2 | 10/2008 | Weers et al. |
| 2003/0108743 A1 | 6/2003 | Anderson |
| 2004/0028619 A1 | 2/2004 | Watanabe et al. |
| 2004/0105820 A1 | 6/2004 | Weers et al. |
| 2005/0003004 A1 | 1/2005 | Vehring et al. |
| 2005/0048127 A1 | 3/2005 | Brown et al. |
| 2005/0148563 A1 | 7/2005 | Cuss et al. |
| 2008/0085315 A1 | 4/2008 | Doney et al. |
| 2010/0016597 A1 | 1/2010 | Hirokawa et al. |
| 2010/0120737 A1 | 5/2010 | Feth et al. |

FOREIGN PATENT DOCUMENTS

| CA | 2 623 560 A1 | 8/2008 |
| CN | 101342155 | 1/2009 |
| EP | 1322301 A1 | 7/2003 |
| JP | 2007-277057 A | 10/2007 |
| WO | 9964014 | 12/1999 |
| WO | 0027363 | 5/2000 |
| WO | 01/76575 A2 | 10/2001 |
| WO | 01/85137 A2 | 11/2001 |
| WO | 02/15876 A2 | 2/2002 |
| WO | 02/28378 A1 | 4/2002 |
| WO | 0245682 | 6/2002 |
| WO | 03/035051 A2 | 5/2003 |
| WO | 03/068944 A1 | 10/2003 |
| WO | 2004/060351 A2 | 7/2004 |
| WO | 2004/098561 A2 | 11/2004 |
| WO | 2004/110404 A1 | 12/2004 |
| WO | 2006010921 | 2/2006 |
| WO | 2007/009164 A1 | 1/2007 |
| WO | 2007/011989 A2 | 1/2007 |
| WO | 2007/077219 A1 | 7/2007 |
| WO | 2007/135409 A1 | 11/2007 |
| WO | 2008/014478 A2 | 1/2008 |
| WO | 2008/066298 A1 | 6/2008 |

OTHER PUBLICATIONS

Friedman et al "A retrospective study of the use of fluticasone propionate/salmeterol combination as initial asthma controller therapy in a commercially insured population" Clin. Ther., Excerpta Medica, vol. 30, No. 10, 2008.
Beier et al "Safety, tolerability and indacaterol, a novel once-daily beta2-agonists, in patents with COPD: a 28 day randomized, placebo controlled clinical trial" Pulm. Pharmacol. & Thera., vol. 20, No. 6, 2007.
Borgstrom et al , Lung deposition of budesonide inhaled via Turbuhaler: a comparison with terbutaline sulphate in normal subjects. Eur Resp J. 1994, 7:69-73.
EMA ICH Topic Q3C Impurities: Guideline for Residual solvents.

*Primary Examiner* — Kevin E Weddington
(74) *Attorney, Agent, or Firm* — Daniel Woods

(57) ABSTRACT

Dry powder formulations for inhalation comprising spray-dried particles and their use in the treatment of an obstructive or inflammatory airways disease. Each particle has a core of a first active ingredient in substantially crystalline form that is coated with a layer of a second active ingredient in substantially amorphous form that is dispersed in a pharmaceutically acceptable hydrophobic excipient. A process for preparing such formulations is also described.

13 Claims, 2 Drawing Sheets

Figure 1:
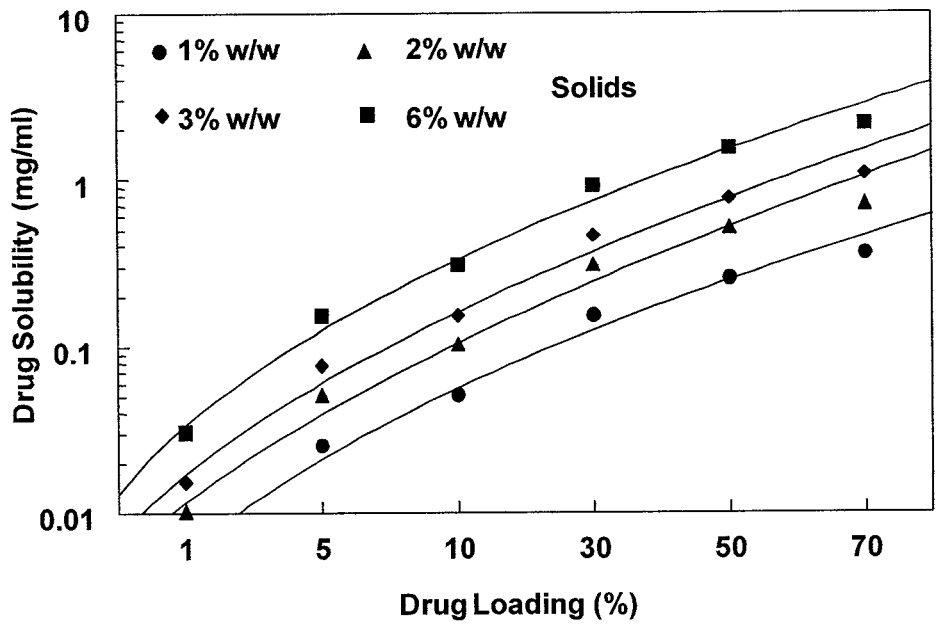
Figure 2:
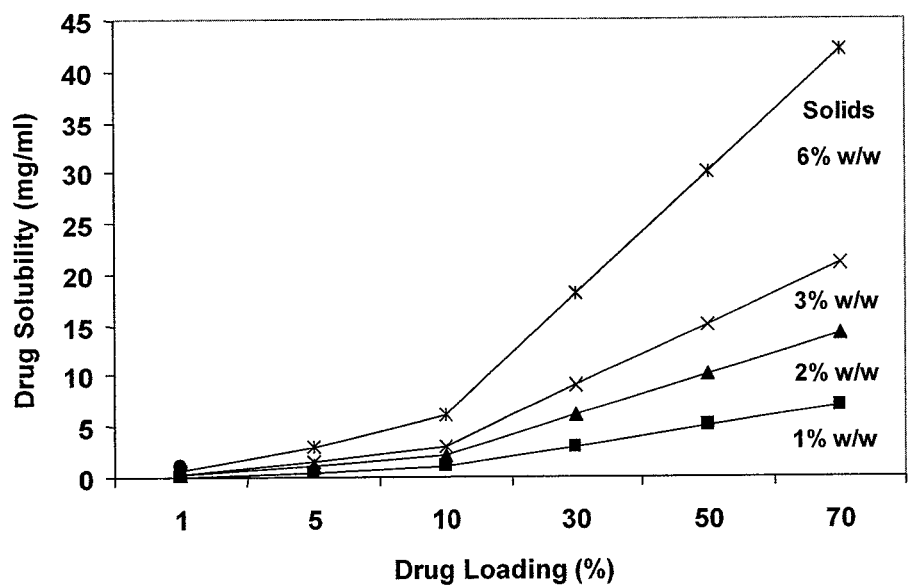

DRY POWDER FORMULATIONS OF PARTICLES THAT CONTAIN TWO OR MORE ACTIVE INGREDIENTS FOR TREATING OBSTRUCTIVE OR INFLAMMATORY AIRWAYS DISEASES

FIELD OF THE INVENTION

This invention relates to organic compounds and their use as pharmaceuticals, more specifically dry powder formulations that comprise spray-dried particles that contain fixed dose combinations of two or more active ingredients that are useful for treating obstructive or inflammatory airways diseases, especially asthma and chronic obstructive pulmonary disease (COPD).

BACKGROUND OF THE INVENTION

Active pharmaceutical ingredients (APIs) that are useful for treating respiratory diseases are generally formulated for administration by inhalation with portable inhalers. The two most popular classes of portable inhalers are pressurized metered dose inhalers (pMDIs) and dry powder inhalers (DPIs).

The vast majority of dry powder inhalers rely on the patient's inspiratory effort to fluidize and disperse the drug particles. In order for the drug to be effectively deposited in the lungs, it is generally accepted that the aerodynamic diameter of the particles must be between 1 μm and 5 μm. As a result APIs are typically micronised to achieve fine particles with a mass median diameter (as determined by laser diffraction) in this size range. Unfortunately fine micronised drug particles generally exhibit poor powder flow, fluidization and dispersion properties. Powder flow or "powder flowability" is the ability of a powder to flow. It is important with respect to metering of the drug particles into a unit dose, either from a reservoir or into pre-packaged unit dose containers (e.g., capsules or blisters). Powder fluidization, which is the mobilization of the powder into the airflow during a patient's inspiration, impacts the delivered dose from the inhaler. Finally, powder dispersion is the break-up of powder agglomerates to primary drug particles. Poor powder dispersion negatively impacts the aerodynamic particle size distribution, and ultimately the delivery of API(s) to the lungs.

Two approaches have been employed in currently marketed products to improve the flow, fluidization and dispersion of fine drug particles.

The first approach involves the controlled aggregation of the undiluted drug to form loosely adherent pellets. The aggregates are formed in rotating blenders with the resulting large particle size distribution providing the required flow properties needed for accurate metering and improved powder fluidization. In the TURBUHALER™ (Astra-Zeneca) device, dispersion of the aggregates occurs by turbulent mixing. The dispersion energy is sufficient under optimal inspiratory flow rates to overcome the interparticle cohesive forces holding the micronised particles together. Because the powder dispersion depends critically on the energy utilized to break up the aggregates, the aerosol performance of pelletized formulations generally exhibits a strong dependence on the patient's inspiratory flow rate. In one study, the total lung deposition for pelletized budesonide was 28% when patients were asked to breathe quickly through the TURBUHALER™ device, and 15% when they were asked to breathe more slowly through the TURBUHALER™ device (see Borgstrom L, Bondesson E, Moren F et al: Lung deposition of budesonide inhaled via TURBUHALER: a comparison with terbutaline sulphate in normal subjects, *European Respiratory Journal*, 1994, 7, 69-73).

The second approach utilises a binary ordered mixture comprising fine drug particles blended with coarse carrier particles. α-Lactose monohydrate has been employed most frequently as the carrier and typically has a particle size between 30 and 90 μm. In most dry powder formulations, drug particles are present in low concentrations, with a drug to carrier ratio of 1:67.5 (w/w), being typical. Micron-sized crystals exhibit forces of attraction, primarily dictated by van der Waals, electrostatic, and capillary forces which are affected by the size, shape, and chemical properties (e.g., surface energy) of the crystal. Unfortunately the adhesive forces between the drug crystals and the carrier are difficult to predict, and may differ for different drugs in a fixed dose combination. During inhalation the drug particles are dispersed from the surface of the carrier particles by the energy of the inspired air flow. The larger carrier particles impact primarily in the oropharynx (i.e. the area of the throat that is at the back of the mouth), whereas the small drug particles penetrate into the lungs.

A key requirement for blend uniformity in an ordered mixture is that the drug and carrier particles interact sufficiently to prevent segregation. Unfortunately, this may reduce pulmonary deposition of the drug, due to poor dispersion of the drug from the carrier. Mean lung deposition for drugs in ordered mixtures is typically 10-30% of the metered dose. The poor lung targeting observed in ordered mixtures results in high deposition in the oropharynx, and the potential for local side-effects, and increased variability. The high variability in lung delivery observed is the result of variability in inertial impaction within the oropharynx, which is a consequence of the powder properties and anatomical differences between subjects. The mean variability in lung dose for micronized drug particle blend formulations is typically between about 30% and 50% (see Olsson B, Borgstrom L: Oropharyngeal deposition of drug aerosols from inhalation products. *Respiratory Drug Delivery*, 2006, pages 175-182). This is exacerbated further when aerosol delivery is dependent on the patient's peak inspiratory flow rate.

The aforementioned issues become especially acute when formulating pharmaceutical products that contain two or more active ingredients in fixed dose combination.

This was illustrated in a recently published study by Taki et al, *Respiratory Drug Delivery* 2006, pages 655-657. The study measured the aerodynamic particle size distributions of the two active ingredients of SERETIDE™, namely salmeterol xinafoate (SX) and fluticasone propionate (FP), as a function of flow rate in an ANDERSEN™ cascade impactor (ACI). The two formulations of SERETIDE™ tested, S100 and S500, refer to differences in the strength of the inhaled corticosteroid (ICS) fluticasone propionate, i.e., 100 μg, and 500 μg. The dose of the long acting $\beta_2$— agonist (LABA) salmeterol xinafoate was held constant at 72.5 μg. The aerodynamic particle size distribution (aPSD) differed significantly for the two active ingredients in the blend formulation (see Table 1). Moreover, the aPSD was dramatically different for the two formulations. Mass median aerodynamic diameters (MMAD) ranged from 1.8 μm to 3.6 μm, geometric standard deviations from 1.7 to 3.9. The ratio of the two active ingredients in the fine particle fraction ($FPF_{<3\ \mu m}$ and $FPF_{<5\ \mu m}$ also differed significantly at the two flow rates tested. Hence, the adhesive properties between the drugs and the carrier differed significantly for each active ingredient and between the formulations as well. The nominal ratio of SX/FP (w/w) in S100 is 0.725, and 0.145 in S500. The ratio of SX/FP in the fine particle dose differs significantly from the nominal ratio, generally enriched in the FP component. The SX/FP ratio varies from +3.5% to −28% of the nominal dose ratios with flow rate and blend ratio. The observed differences are probably the result of differences in the API particle size distribution and differences in the dose ratios that may result from inadequate mixing. Furthermore, one API may have lower affinity for the carrier, and may segregate in the formulation at any stage in the manufacturing process. Moisture uptake may also differ for the two APIs, leading to differences in agglomeration on storage. All of these factors taken in total dramatically increase the complexity of the development process, and the overall variability in drug delivery.

TABLE 1

Aerodynamic particle size distributions of fixed dose combinations of salmeterol xinafoate and fluticasone propionate formulated as ordered mixtures with coarse lactose monohydrate (Taki et al. Respiratory Drug Delivery 2006, pp. 655-657)

|  |  |  | Mean (n = 4) | | | |
|---|---|---|---|---|---|---|
|  |  |  | MMAD (μm) | GSD | FPF < 3 μm (%) | FPF < 5 μm (%) |
| Q = 30 LPM | S100 | SX | 3.6 | 1.9 | 10.3 | 18.2 |
|  |  | FP | 3.2 | 2.1 | 14.5 | 22.9 |
|  |  | t-test (p-value) SX vs. FP | 0.030 | 0.440 | 0.013 | 0.011 |
|  |  | SX/FP (% from nominal) |  |  | 0.52 (−28%) | 0.58 (−20%) |
|  | S500 | SX | 2.8 | 1.8 | 12.9 | 19.9 |
|  |  | FP | 2.7 | 1.8 | 17.3 | 25.9 |
|  |  | t-test (p-value) SX vs. FP | 0.250 | 0.470 | 0.015 | 0.005 |
|  |  | SX/FP |  |  | 0.11 (−24%) | 0.11 (−24%) |
| Q = 66 LPM | S100 | SX | 1.9 | 2.5 | 22.0 | 26.9 |
|  |  | FP | 2.1 | 2.0 | 21.3 | 27.0 |
|  |  | t-test (p-value) SX vs. FP | 0.018 | 0.170 | 0.318 | 0.898 |
|  |  | SX/FP |  |  | 0.75 (+3.5%) | 0.72 (−0.7%) |
|  | S500 | SX | 1.8 | 3.9 | 17.6 | 21.3 |
|  |  | FP | 2.1 | 1.7 | 21.2 | 26.6 |
|  |  | t-test (p-value) SX vs. FP | 0.304 | 0.370 | 0.007 | 0.001 |
|  |  | SX/FP |  |  | 0.12 (−17%) | 0.12 (−17%) |

In order to circumvent the problem of the formulation of multiple active ingredients in a single blend, devices (e.g. the GEMINI device of WO 05/14089) are known which incorporate two separate blisters containing each independent drug blend, which is then actuated concurrently. While such device options for combination therapy may minimize potential interactions between the active ingredients and the device components, they do nothing to solve other inherent drug targeting and variability issues associated with lactose blends. Hence, a need exists for improved formulations which overcome the dosing issues associated with blends of multiple active ingredients, and which provide for improvements in dose consistency and lung targeting. The need is especially acute for APIs with vastly different physicochemical properties (e.g., solubility), where finding a common solvent for particle engineering is problematic.

It has now been found that inhalable dry powder formulations that contain two or more active ingredients and yet have desirable fluidization and dispersion properties of drug particles may be prepared by engineering the active ingredients within inhalable spray-dried particles.

SUMMARY OF THE INVENTION

In a first aspect the present invention relates to a dry powder formulation for inhalation comprising spray-dried particles that comprise a core of a first active ingredient in substantially crystalline form that is coated with a layer of a second active ingredient in substantially amorphous form that is dispersed in a pharmaceutically acceptable hydrophobic excipient.

The first active ingredient, second active ingredient and hydrophobic excipient are substantially phase separated in the spray-dried particles.

Such a formulation having particles that are structured or "engineered" in this way eliminates the significant differences in aerodynamic particle size distribution and fine particle dose that occur when the same active ingredients are formulated as ordered mixtures. The particles also exhibit improved lung targeting (e.g., higher lung delivery efficiency, reduced oropharyngeal and systemic deposition), and improved dose consistency (via reduced inter-patient variability and flow rate dependence) relative to standard lactose blends and pelletized formulations.

The active ingredients can be any active pharmaceutical ingredients that are useful for treating obstructive or inflammatory airways diseases, particularly asthma and COPD. Suitable active ingredients include long acting $\beta_2$-agonists such as salmeterol, formoterol, indacaterol and salts thereof, muscarinic antagonists such as tiotropium and glycopyrronium and salts thereof, and corticosteroids including budesonide, ciclesonide, fluticasone and mometasone and salts thereof. Suitable combinations include (formoterol fumarate and budesonide), (salmeterol xinafoate and fluticasone propionate), (salmeterol xinafoate and tiotropium bromide) and (indacaterol maleate and glycopyrronium bromide).

The presence of amorphous drug domains in crystalline micronized drugs for inhalation is generally thought to be undesirable. Amorphous domains are thermodynamically unstable, and may convert to a stable crystalline polymorph over time. The recrystallization process often results in coarsening of the micronized drug particles and decreased aerosol performance. The higher energy amorphous domains may also exhibit greater solubility, more rapid dissolution, and decreased chemical stability as compared to the crystalline drug. As a result, it is general practice to attempt to reduce the amorphous content in micronized drug particles, and companies go to great lengths to "condition" powders to reduce amorphous content.

Spray drying is a method of producing a dry powder from a liquid or a dispersion in a liquid by rapidly drying with a hot gas. Its principal advantages for producing engineered particles for inhalation include the ability to rapidly produce a dry powder, and to control particle attributes including size, morphology, density, and surface composition. The drying process is very rapid (on the order of milliseconds). As a result most active pharmaceutical ingredients which are dissolved in the liquid phase precipitate as amorphous solids, as they do not have time to crystallize.

For fixed dose combinations it is common practice to attempt to find a common solvent where both drugs are soluble. Formulating two drugs in a single amorphous phase invites potential incompatibility issues. One of the drugs is likely to have improved physical and chemical stability, while the other will have reduced stability.

When designing aerosol formulations comprising fixed dose combinations of two or more drugs, it is not always possible to identify a solvent in which each drug is miscible or immiscible. Hence, to formulate fixed dose combinations of these drugs it may be necessary to spray-dry a complex dispersion of one drug in solution and another in suspension. This results in crystalline and amorphous domains in the spray-dried drug product. It has been surprisingly discovered that stable formulations comprising these crystalline and amorphous drug domains can be achieved. By incorporation of a hydrophobic excipient which is effectively concentrated at the particle interface, it becomes possible to also control the surface energy and morphology of the spray-dried particles resulting in reduced interparticle cohesive forces and enhanced aerosol performance.

A third active ingredient may be introduced into the particle, either as an additional insoluble crystalline active ingredient, or as an additional amorphous active ingredient. The third active ingredient may be selected, for example, from bronchodilators, anti-inflammatories, and mixtures thereof, especially $\beta_2$-agonists, muscarinic antagonists, steroids, dual $\beta_2$-agonist-muscarinic antagonists, PDE4 inhibitors, $A_{2A}$ agonists, calcium blockers and mixtures thereof. Suitable triple combinations include (salmeterol xinafoate, fluticasone propionate and tiotropium bromide), (indacaterol maleate, mometasone furoate and glycopyrronium bromide), and (indacaterol acetate, mometasone furoate and glycopyrronium bromide).

In a second aspect the present invention relates to a process for preparing a dry powder formulation of spray-dried particles that contain a first active ingredient and a second active ingredient, the process comprising the steps of:

(a) preparing a feedstock comprising the second active ingredient dissolved in a solvent phase, a hydrophobic excipient, and crystalline particles of the first active ingredient, said crystalline particles being substantially insoluble in said solvent phase; and (b) spray-drying said feedstock to provide the formulation, wherein said particles comprise a core of the first active ingredient in substantially crystalline form that is coated with a layer of the second active ingredient in substantially amorphous form that is dispersed in a pharmaceutically acceptable hydrophobic excipient.

In a preferred embodiment the solvent phase is water or a mixture of ethanol and water.

In a third aspect the present invention relates to a method for the treatment of an obstructive or inflammatory airways disease which comprises administering to a subject in need thereof an effective amount of the aforementioned dry powder formulation. The obstructive or inflammatory airways disease is suitably asthma or COPD.

In a fourth aspect the present invention relates to the use of the aforementioned dry powder formulation in the manufacture of a medicament for the treatment of an obstructive or inflammatory airways disease. The obstructive or inflammatory airways disease is suitably asthma or COPD.

In a fifth aspect the present invention relates to the aforementioned dry powder formulation for use in the treatment of an obstructive or inflammatory airways disease. The obstructive or inflammatory airways disease is suitably asthma or COPD.

In a sixth aspect the present invention relates to a delivery system that comprises an inhaler that contains the aforementioned dry powder formulation.

A seventh aspect of the present invention comprises any two or more of the foregoing aspects, embodiments or features.

TERMS

Terms used in the specification have the following meanings:

"Active ingredient" or "drug" as used herein means the active ingredient of a pharmaceutical, also known as an active pharmaceutical ingredient (API).

"Amorphous" as used herein refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ("glass transition").

"Crystalline" as used herein refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ("melting point"). In the context of the present invention, a crystalline active ingredient means an active ingredient with crystallinity of greater than 85%. In certain embodiments the crystallinity is suitably greater than 90%. In other embodiments the crystallinity is suitably greater than 95%.

"Delivered dose" or "DD" as used herein refers to an indication of the delivery of dry powder from an inhaler device after an actuation or dispersion event from a powder unit. DD is defined as the ratio of the dose delivered by an inhaler device to the nominal or metered dose. The DD is an experimentally determined parameter, and may be determined using an in vitro device set up which mimics patient dosing. It is sometimes also referred to as the emitted dose (ED).

"Fine particle fraction" or "FPF" as used herein means the mass of an active ingredient below a specified minimum aerodynamic size relative to the nominal dose. For example, $FPF_{<3.3\ \mu m}$ refers to the percentage of the nominal dose which has an aerodynamic particle size less than 3.3 μm. FPF values are determined using cascade impaction, either on an ANDERSEN™ cascade impactor, or a NEXT GENERATION IMPACTOR™ cascade impactor. In order to minimize interpatient variability and improve lung targeting, it is preferred that a fine particle fraction less than 3.3 μm (FPF$_{<3.3\mu m}$) of greater than 40% w/w of the nominal dose be achieved.

"Fixed dose combination" as used herein refers to a pharmaceutical product that contains two or more active ingredients that are formulated together in a single dosage form available in certain fixed doses.

"Mass median diameter" or "MMD" or "x50" as used herein means the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. In certain embodiments of the present invention the inhalable medicament particles have a MMD of between 1 and 10 microns.

"Mass median aerodynamic diameter" or "MMAD" as used herein refer to the median aerodynamic size of a plurality of particles, typically in a polydisperse population. The "aerodynamic diameter" is the diameter of a unit density sphere having the same settling velocity, generally in air, as a powder and is therefore a useful way to characterize an aerosolized powder or other dispersed particle or particle formulation in terms of its settling behavior. MMAD is determined herein by cascade impaction. In one or more embodiments, a powder of the present invention comprises a mass median aerodynamic diameter from about 1 μm to 5 μm, such as about 1.5 μm to about 4.0 μm, or about 2.0 μm to 4.0 μm. In general, if the particles are too large, fewer particles will reach the deep lung. If the particles are too small, a larger percentage of the particles may be exhaled. In certain embodiments of the present invention the inhalable medicament particles have a MMAD from 1 to 5 microns.

"Rugous" as used herein means having numerous wrinkles or creases, i.e. being ridged or wrinkled.

"Rugosity" as used herein is a measure of the surface roughness of an engineered particle. For the purposes of this invention, rugosity is calculated from the specific surface area obtained from BET measurements, true density obtained from helium pycnometry, and the surface to volume ratio obtained by laser diffraction (Sympatec), viz:

$$\text{Rugosity} = (SSA \cdot \rho_{true})/S_v$$

where $S_v = 6/D_{32}$, where $D_{32}$ is the average diameter based on unit surface area. Increases in surface roughness are expected to reduce interparticle cohesive forces, and improve targeting of aerosol to the lungs. Improved lung targeting is expected to reduce interpatient variability, and levels of drug in the oropharynx and systemic circulation. In one or more embodiments, the rugosity $S_v$ is from 3 to 20, e.g. from 5 to 10.

"Insoluble" as used herein means having a solubility in the solvent of less than 1 mg/ml. In certain embodiments of the present invention the solubility, or example of the active ingredient, is suitably less than 0.1 mg/ml, or preferably less than 0.01 mg/ml.

"Soluble" as used herein means having a solubility in the solvent of 1 mg/ml or greater. In certain embodiments of the present invention the solubility, for example of the active ingredient, is suitably greater than 10 mg/ml, or preferably greater than 20 mg/ml).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

The entire disclosure of each United States patent and international patent application mentioned in this patent specification is fully incorporated by reference herein for all purposes.

DETAILED DESCRIPTION OF THE DRAWINGS

The dry powder formulation of the present invention may be described with reference to the accompanying drawings. In those drawings:

FIG. 1 is a plot of the required drug solubility for the "insoluble" API to achieve a total dissolved fraction of less than 5% w/v in the feedstock as a function of drug loading and solids content. Soluble drug is expected to be converted to an amorphous solid in the spray-dried particles.

FIG. 2 is a plot of the required drug solubility for the "soluble" API to be completely miscible in the feedstock as a function of variations in drug loading and solids content.

FIG. 3 shows wide-angle X-ray powder diffraction patterns of: (a) a spray-dried vehicle formulation comprising a 2:1 mol:mol ratio of DSPC:$CaCl_2$; (b) micronized crystalline indacaterol API (QAB149); (c) spray-dried formulation comprising 6% w/w indacaterol (QAB149) and 2% w/w glycopyrrolate (NVA237); (d) spray-dried formulation comprising 45% indacaterol (QAB149) and 15% glycopyrrolate (NVA237). The powder patterns of the spray-dried fixed dose combination products illustrate that the two drugs and hydrophobic excipient are phase-separated in distinct domains: indacaterol is present in crystalline form, glycopyrrolate is present as an amorphous solid, and DSPC is present in a phospholipid gel phase.

DETAILED DESCRIPTION OF THE INVENTION

The present invention concerns dry powder formulations for inhalation comprising spray-dried particles. Those spray-dried particles comprise fixed dose combinations of two or more active ingredients that are suitable for treating obstructive or inflammatory airways diseases, particularly asthma and COPD.

In one aspect or embodiment, the spray-dried particles comprise a first active ingredient that is in substantially crystalline form, a second active ingredient in substantially amorphous form, and a pharmaceutically acceptable hydrophobic excipient, wherein the three materials are substantially phase separated in the spray-dried particles. The particles can therefore be described as being "structured" or "engineered".

The active ingredients can be any active pharmaceutical ingredients that are useful for treating obstructive or inflammatory airways diseases, particularly asthma and COPD. They may be selected, for example, from bronchodilators, anti-inflammatories, and mixtures thereof, especially $\beta_2$-agonists, muscarinic antagonists, steroids, dual $\beta_2$-agonist-muscarinic antagonists, PDE4 inhibitors, $A_{2A}$ agonists, calcium blockers and mixtures thereof.

Suitable active ingredients include $\beta_2$-agonists. Suitable $\beta_2$-agonists include arformoterol (e.g. tartrate), albuterol/salbutamol (e.g. racemate or single enantiomer such as the R-enantiomer, or salt thereof especially sulfate), AZD3199, bambuterol, BI-171800, bitolterol (e.g. mesylate), carmoterol, clenbuterol, etanterol, fenoterol (e.g. racemate or single enantiomer such as the R-enantiomer, or salt thereof especially hydrobromide), flerbuterol, formoterol (e.g. racemate or single diastereomer such as the R,R-diastereomer, or salt thereof especially fumarate or fumarate dihydrate), GSK-159802, GSK-597901, GSK-678007, indacaterol (e.g. racemate or single enantiomer such as the R-enantiomer, or salt thereof especially maleate, acetate or xinafoate), LAS100977, metaproterenol, milveterol (e.g. hydrochloride), naminterol, olodaterol (e.g. racemate or single enantiomer such as the R-enantiomer, or salt thereof especially hydrochloride), PF-610355, pirbuterol (e.g. acetate), procaterol, reproterol, salmefamol, salmeterol (e.g. racemate or single enantiomer such as the R-enantiomer, or salt thereof especially xinafoate), terbutaline (e.g. sulphate) and vilanterol (or a salt thereof especially trifenatate. In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol.

In a preferred embodiment one of the active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids such as formic acid, acetic acid, propionic acid, butyric acid, benzoic acid, o-hydroxybenzoic acid, p-hydroxybenzoic acid, p-chlorobenzoic acid, diphenylacetic acid, triphenylacetic acid, 1-hydroxynaphthalene-2-carboxylic acid, 3-hydroxynaphthalene-2-carboxylic acid, aliphatic hydroxy acids such as lactic acid, citric acid, tartaric acid or malic acid, dicarboxylic acids such as fumaric acid, maleic acid or succinic acid, and sulfonic acids such as methanesulfonic acid or benzenesulfonic acid. These salts may be prepared from the compound by known salt-forming procedures. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate. Other useful salts include the hydrogen succinate, fumarate, hippurate, mesylate, hydrogen sulphate, hydrogen tartrate, hydrogen chloride, hydrogen bromide, formate, esylate, tosylate, glycolate and hydrogen malonate salts, which, like the acetate and xinafoate salts, are disclosed in international patent application WO 2008/000839 together with methods of their respective preparation.

Suitable active ingredients include muscarinic antagonists or antimuscarinics. Suitable muscarinic antagonists include aclidinium (e.g. bromide), BEA-2108 (e.g. bromide), BEA-2180 (e.g. bromide), CHF-5407, darifenacin (e.g. bromide), darotropium (e.g. bromide), glycopyrrolate (e.g. racemate or single enantiomer, or salt thereof especially bromide), dexpirronium (e.g. bromide), iGSK-202405, GSK-203423, GSK-573719, GSK-656398, ipratropium (e.g. bromide), LAS35201, LAS186368, otilonium (e.g. bromide), oxitropium (e.g. bromide), oxybutynin, PF-3715455, PF-3635659, pirenzepine, revatropate (e.g. hydrobromide), solifenacin (e.g. succinate), SVT-40776, TD-4208, terodiline, tiotropium (e.g. bromide), tolterodine (e.g. tartrate), and trospium (e.g. chloride). In certain preferred embodiments the muscarinic antagonists is long-acting muscarinic antagonist such as darotropium bromide, glycopyrrolate or tiotropium bromide.

In a preferred embodiment one of the active ingredients is a glycopyrronium salt. Glycopyrronium salts include glycopyrronium bromide, also known as glycopyrrolate, which is known to be an effective antimuscarinic agent. More specifically it inhibits acetyl choline binding to M3 muscarinic receptors thereby inhibiting bronchoconstriction. glycopyrrolate is a quaternary ammonium salt. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate. Glycopyrrolate can be prepared using the procedures described in U.S. Pat. No. 2,956,062. It has two stereogenic centres and hence exists in four isomeric forms, namely (3R,2'R)-, (3S,2'R)-, (3R,2'S)- and (3S,2'S)-3-[(cyclopentyl-hydroxyphenyl-acetyl)oxy]-1,1-dimethylpyrrolidinium bromide, as described in United States patent specifications U.S. Pat. No. 6,307,060 and U.S. Pat. No. 6,613,795. When the drug substance of the dry powder formulation is glycopyrrolate, it can be one or more of these isomeric forms, especially the 3S,2'R isomer, the 3R,2'R isomer or the 2S,3'R isomer, thus including single enantiomers, mixtures of diastereomers, or racemates, especially (3S,2'R/3R,2'S)-3-[(cyclopentyl-hydroxy-phenylacetyl)oxy]-1,1-dimethylpyrrolidinium bromide. R,R-glycopyrrolate is also known as dexpirronium.

Suitable active ingredients include bifunctional active ingredients such as dual$\beta_2$-agonists-muscarinic antagonists. Suitable dual $\beta_2$-agonists-muscarinic antagonists include GSK-961081 (e.g. succinate).

Suitable active ingredients include steroids, for example corticosteroids. Suitable steroids include budesonide, beclamethasone (e.g. dipropionate), butixocort (e.g. propionate), CHF5188, ciclesonide, dexamethasone, flunisolide, fluticasone (e.g. propionate or furoate), GSK-685698, GSK-870086, LAS40369, methyl prednisolone, mometasone (e.g. furoate), prednisolone, rofleponide, and triamcinolone (e.g. acetonide). In certain preferred embodiments the steroid is long-acting corticosteroids such as budesonide, ciclesonide, fluticasone or mometasone.

In a preferred embodiment one of the active ingredients is mometasone (i.e. (11β,16α)-9,21-dichloro-17-[(2-furanylcarbonyl)oxy]-11-hydroxy-16-methylpregna-1,4-diene-3,20-dione, alternatively designated 9α,21-dichloro-16α-methyl-1,4-pregnadiene-11β,17α-diol-3,20-dione 17-(2'-furoate)) or a salt thereof, for example mometasone furoate and mometasone furoate monohydrate. Mometasone furoate and its preparation are described in U.S. Pat. No. 4,472,393. It use in the treatment of asthma is described in U.S. Pat. No. 5,889,015. It use in the treatment of other respiratory diseases is described in U.S. Pat. Nos. 5,889,015, 6,057,307, 6,057,581, 6,677,322, 6,677,323 and 6,365,581.

Pharmaceutically acceptable esters, acetals, and salts of the above therapeutics are contemplated. The determination of the appropriate esters, acetals, or salt form is driven by the duration of action and tolerability/safety data. As well, API selection may be important from the standpoint of selecting therapeutics with the appropriate physical properties (e.g., solubility) to achieve the embodiments of the present invention.

Suitable combinations include those that contain a $\beta_2$-agonist and a corticosteroid, for example (carmoterol and budesonide), (formoterol and beclomethasone), (formoterol fumarate and budesonide), (formoterol fumarate dihydrate and mometasone furoate), (formoterol fumarate and ciclesonide), (indacaterol maleate and mometasone furoate), (indacaterol acetate and mometasone furoate), (indacaterol xinafoate and mometasone furoate), (milveterol hydrochloride and fluticasone), (olodaterol hydrochloride and fluticasone furoate), (olodaterol hydrochloride and mometasone furoate), (salmeterol xinafoate and fluticasone propionate), (vilanterol trifenatate and fluticasone furoate), and (vilanterol trifenatate and mometasone furoate); a $\beta_2$-agonist and a muscarinic antagonist, for example (formoterol and aclidinium bromide), (indacaterol and darotropium), (indacaterol maleate and glycopyrrolate); (indacaterol maleate and GSK573719), (milveterol hydrochloride and glycopyrrolate), (milveterol hydrochloride and tiotropium bromide), olodaterol hydrochloride and glycopyrrolate), (olodaterol hydrochloride and tiotropium bromide), (salmeterol xinafoate and tiotropium bromide), (vilanterol trifenatate and darotropium), (vilanterol trifenatate and glycopyrrolate), (vilanterol trifenatate and GSK573719), and (vilanterol trifenatate and tiotropium bromide); and a muscarinic antagonist and a corticosteroid, for example (glycopyrrolate and mometasone furoate), and (glycopyrrolate and ciclesonide); or a dual $\beta_2$-agonist-muscarinic antagonist and a corticosteroid, for example (GSK-961081 succinate and mometasone furoate), (GSK-961081 succinate and mometasone furoate monohydrate), and (GSK-961081 succinate and ciclesonide)

The spray-dried particles of the dry powder formulation of the present invention may contain three active ingredients. In a suitable embodiments the third active ingredient in those particles is substantially crystalline. In other suitable embodiments the third active ingredient in those particles is substantially amorphous and is mixed with the amorphous phase of the second active ingredient.

Suitable triple combinations include those that contain a $\beta_2$-agonist, a muscarinic antagonist and a corticosteroid, for example (salmeterol xinafoate, fluticasone propionate and tiotropium bromide), (indacaterol maleate, mometasone furoate and glycopyrrolate) and (indacaterol acetate, mometasone furoate and glycopyrrolate).

Active ingredients may exist in a continuum of solid states ranging from fully amorphous to fully crystalline. For the purposes of the present invention an active ingredient is in substantially crystalline form when it has a crystallinity of greater than 85%. In certain embodiments the crystallinity is suitably greater than 90%. In other embodiments the crystallinity is suitably greater than 95%, for example greater than 99%.

The first active ingredient is substantially crystalline. The first active ingredient should also be substantially insoluble in the solvent that is used to prepare the feedstock that is spray-dried to form the particles. For the purposes of the present invention, the first active ingredient has a solubility of less than about 1 mg/ml, for example less than 0.05 mg/ml. In certain embodiments, the first active ingredient has a solubility of less than 0.01 mg/ml, for example less than 0.005 mg/ml. The proposed limits on the solubility are driven by the desire to minimize the percentage of drug which dissolves in the solvent phase, and subsequently ends up as an amorphous solid in the spray-dried powder.

The second active ingredient, which is soluble in the solvent to be spray-dried, is present in substantially amorphous form in the spray-dried particles. It should be noted that the second active ingredient is in this form when the particles have been formed. The second active ingredient can have a substantially amorphous or a substantially crystalline form when the active ingredient is received. The physical form of the second active ingredient and the particle size of that ingredient are irrelevant when preparing the feedstock since the second active ingredient is dissolved in the solvent. The rapid drying provided by the spray-drier causes the second active ingredient to have a substantially amorphous form. The first active ingredient retains its crystalline form during the drying process since it is substantially insoluble in the solvent that is used in the feedstock.

For the purposes of the present invention an active ingredient is in substantially amorphous form when it has a crystallinity of less than 15%. In certain embodiments the crystallinity is suitably less than 10%. In other embodiments the crystallinity is suitably less than 5%, for example less than 2% or less than 1%.

For the purposes of the present invention a hydrophobic excipient is included in the formulation. By careful control of the formulation and process, it is possible for the surface of the spray-dried particles to be comprised primarily of the hydrophobic excipient. Surface concentrations in excess of 70% are contemplated. In certain embodiments the surface is comprised of greater than 90% hydrophobic excipient, or greater than 95% hydrophobic excipient, for example greater than 98% hydrophobic excipient or greater than 99% hydrophobic excipient.

In certain preferred embodiments the hydrophobic excipient facilitates development of a rugous particle morphology. This means the particle morphology is wrinkled and creased rather than smooth. This means the interior and/or the exterior surface of the inhalable medicament particles are at least in part rugous. This rugosity is useful for providing dose consistency and drug targeting by improving powder fluidization and dispersibility. While not wanting to be bound by theory, increases in particle rugosity result in decreases in interparticle cohesive forces as a result of an inability of the particles to approach to within van der Waals contact. The decreases in cohesive forces are sufficient to dramatically improve powder fluidization and dispersion in ensembles of rugous particles.

The rugosity of the particles may be increased by using a pore-forming agent, such as perflubron, during their manufacture, or by controlling the formulation and/or process to produce rugous particles.

The hydrophobic excipient may take various forms that will depend at least to some extent on the composition and intended use of the dry powder formulation. Suitable pharmaceutically acceptable hydrophobic excipients may, in general, be selected from the group consisting of long-chain phospholipids, hydrophobic amino acids and peptides, and long chain fatty acid soaps.

Phospholipids from both natural and synthetic sources may be used in varying amounts. When phospholipids are present, the amount is typically sufficient to provide a porous coating matrix of phospholipids. If present, phospholipid content generally ranges from about 40 to 99% w/w of the medicament, for example 70% to 90% w/w of the medicament. The high percentage of excipient is also driven by the high potency and therefore typically small doses of the active ingredients. Given that no carrier particle is present in the spray-dried particles, the excipients also serve as bulking agents in the formulation, enabling effective delivery of low dose therapeutics. In some embodiments, it is also desirable to keep the drug loading low to ensure that the particle properties are controlled by the surface composition and morphology of the particles. This enables comparable physical stability and aerosol performance between mono and combination particles to be achieved.

The minimum fill mass of fine powder that can be reasonably filled commercially with a relative standard deviation of less than 3% is about 0.5 mg. In contrast, the required lung dose of active ingredients may be as low as 0.01 mg, and routinely is about 0.2 mg or less. Hence, significant quantities of excipient are required. In instances, where the drugs are less potent, it may be possible to decrease the required content of the excipients, although keeping the excipient concentration high enables control of the surface composition and particle morphology, attributes deemed critical in achieving equivalent performance between the mono-component and fixed dose combination formulations. It should be kept in mind, however, that low drug loadings increase the potential for the crystalline active ingredient to dissolve in the solvent to be spray-dried. Care should be taken to minimize dissolution of the crystalline active ingredient to the extent possible.

Generally compatible phospholipids comprise those having a gel to liquid crystal phase transition greater than about 40° C., such as greater than 60° C., or greater than about 80° C. The incorporated phospholipids may be relatively long chain (e.g., $C_{16}$-$C_{22}$) saturated phospholipids. Exemplary phospholipids useful in the disclosed stabilized preparations include, but are not limited to, phosphatidylcholines, such as dipalmitoylphosphatidylcholine (DPPC), distearoylphosphatidylcholine (DSPC), and hydrogenated egg or soy phosphatidylcholines (e.g., E-100-3, S-100-3, available from Lipoid KG, Ludwigshafen, Germany). Natural phospholipids are preferably hydrogenated, with a low iodine value (<10).

The phospholipids may optionally be combined with cholesterol to modify the fluidity of the phospholipid acyl chains.

The long-chain phospholipids may optionally be combined with a divalent metal ion (e.g. calcium, magnesium). Such a divalent metal ion acts to decrease headgroup hydration, thereby increasing the phospholipid gel to liquid crystal phase transition, and the wettability of the powders on lung lining fluid. The molar ratio of polyvalent cation to phospholipid may be at least about 0.05:1, such as about 0.05:1 to 0.5:1. In one or more embodiments; a molar ratio of polyvalent cation:phospholipid is 0.5:1. While not wanting to be bound by theory, it is believed that the divalent metal ion binds to the phosphate groups on the zwitterionic phosphatidylcholine headgroup, displacing water molecules in the process. Molar ratios of metal ion to phospholipid in excess of 0.5 may result in free metal ion not bound to the phosphate groups. This can significantly increase the hygroscopicity of the resulting dry powder and is not preferred. When the polyvalent metal ion is calcium, it may be in the form of calcium chloride. Although metal ions, such, as calcium, are often included with phospholipids, none is required, and their use can be problematic when other ions are present in the formulation (e.g., phosphate, which may precipitate the calcium ions as calcium phosphate). When compatibility issues occur, there may be benefit in using $Mg^{++}$ salts, as they typically have $K_{sp}$ values which are three to four orders of magnitude higher than $Ca^{++}$ salts.

The hydrophobic excipient may also comprise long chain fatty acid soaps. The alkyl chain length is generally 14-22 carbons in length with saturated alkyl chains preferred. The fatty acid soaps may utilize monovalent (e.g., $Na^+$, $K^+$) or divalent counterions (e.g., $Ca^{++}$, $Mg^{++}$). Particularly preferred fatty acid soaps are sodium stearate and magnesium stearate. The solubility of fatty acid soaps may be increased above the Krafft point. Potassium salts of fatty acids generally have the lowest Krafft point temperature, and greater aqueous solubility at a given temperature. Calcium salts are expected to have the lowest solubility. The hydrophobic fatty acid soaps provide a wax-like coating on the particles. The proposed loadings in the spray-dried particles are similar to the phospholipids detailed previously.

The hydrophobic excipient may also comprise hydrophobic amino acids, peptides, or proteins. Particularly preferred are the amino acid leucine, and its oligomers dileucine and trileucine. Proteins, such as, human serum albumin are also contemplated. Trileucine is particularly preferred, as its solubility profile and other physicochemical properties (e.g., surface activity, log P) facilitate creation of core-shell particles, where trileucine controls the surface properties and morphology of the resulting particles.

The dry powder formulation of the present invention may additionally comprise one or more excipients.

The amorphous phase may optionally contain additional glass-forming excipients chosen so as to: increase the glass transition temperature, $T_g$, and relaxation time of the amorphous phase. Preferred glass forming materials are selected from sugars (e.g., sucrose, trehalose, lactose) sugar alcohols (e.g., mannitol), amino acids/peptides (e.g., leucine), and salts/buffers (e.g., sodium citrate, sodium maleate). Particularly preferred glass-forming excipients are those with a $T_g$>100° C. (e.g., sodium citrate, inulin, and trehalose). The water soluble glass forming excipients are chosen such that they will diffuse rapidly away from the interface during the drying process, enabling enrichment of the particle surface with the hydrophobic excipient. In such a particle, the particle properties will be controlled to a significant extent by the surface composition/morphology. The surface composition of the particles is comprised of greater than 70% w/w of the hydrophobic excipient, more often greater than 90% w/w, or 95% w/w. The morphology of the particles (asperities or pores) and the ability to create core-shell particles is controlled by the composition of the feedstock, and its drying properties as characterized by the Peclet numbers of each component, throughout the drying process.

The amount of the glass-forming excipient required will be determined by the glass transition temperatures of the drug substance to be stabilized, and the glass stabilizing agent. The goal is to achieve a $T_g$ for the drug product which is at least 80° C. The Fox equation can be utilized to estimate the quantity of glass-forming excipient required to achieve this target, viz:

$$\frac{1}{T_g} = \frac{w_1}{T_{g(1)}} + \frac{w_2}{T_{g(2)}}$$

Where $w_1$ and $w_2$ are the weight fractions of the drug and glass forming excipient, respectively. Care must be taken with sodium citrate to avoid precipitation with divalent ions which may be present with the hydrophobic shell-forming excipients. In these cases, the use of trehalose or inulin may be preferred. Table 2 provides a list of common glass-forming materials, and their representative dry $T_g$ values.

TABLE 2

Dry Tg values of some common glass-forming excipients and related materials

| Excipient | Dry $T_g$ (° C.) |
| --- | --- |
| glycerol | −93 |
| sorbitol | −3 |
| fructose | 13 |
| glucose | 38 |
| maltose | 101 |

TABLE 2-continued Dry Tg values of some common glass-forming excipients and related materials

| Excipient | Dry $T_g$ (° C.) |
|---|---|
| sucrose | 73 |
| trehalose | 117 |
| raffinose | 104 |
| lactose | 112 |
| mannitol | 11 |
| sodium citrate | 170 (pH > 7) |
| maltohexose | 173 |
| leucine | 140 |
| trileucine | 70-100 (pH dependent) |

In one or more embodiments of the dry powder formulation of the present invention, the excipient may additionally or alternatively include additives to further enhance stability or biocompatibility of the formulation. For example, various salts, buffers, chelators, and taste masking agents are contemplated. The use of these additives will be understood to those of ordinary skill in the art and the specific quantities, ratios, and types of agents can be determined empirically without undue experimentation.

In one or more embodiments, the dry powder formulation of the present invention is prepared by a two step process.

In the first step of the process for preparing a dry powder formulation of spray-dried particles that contain a first active ingredient and a second active ingredient, a feedstock is prepared that comprises the second active ingredient dissolved in a solvent phase, a hydrophobic excipient, and crystalline particles of the first active ingredient. The crystalline particles of the first active ingredient are substantially insoluble in the solvent phase in order to minimise the presence of the first active ingredient in the amorphous phase.

The choice of solvent depends on the physicochemical properties of the active ingredients. Useful solvents from which to make a selection include water, ethanol, ethanol/water, acetone, dichloromethane, dimethylsulfoxide, and other Class 3 solvents as defined in ICH Q3C Guidelines, for example ICH Topic Q3C(R4) Impurities: Guideline for Residual Solvents (European Medicines Agency reference CPMP/ICH/283/95 of February 2009).

In certain preferred embodiments the first active ingredient is poorly soluble in water so suitable solvents are water and water mixed with ethanol. When the first active ingredient is indacaterol the solvent is preferably water.

According to FIG. 1, the API solubility required to achieve a dissolved fraction of the first active ingredient of 5% w/w or less increases with increases in drug loading, and solids content of the feedstock to be spray-dried. At the preferred drug loadings (i.e., <30%), the drug solubility must be less than 1 mg/ml, preferably less than 0.01 mg/ml.

The solubility of first active ingredient in the feedstock to be spray-dried can be decreased by decreasing the temperature of the feedstock. As a rule of thumb, solubility decreases two-fold with each 10° C. decrease in temperature. Hence, going from room temperature to refrigerated conditions would be expected to decrease solubility about 4-fold.

In some instances, the addition of salts which "salt out" the active ingredient may be utilized to further expand the range of insoluble active ingredients that can be prepared within the context of the invention. It may also be possible to modify the pH or add common ions for active ingredients with ionisable groups to limit solubility according to Le Chatelier's Principle.

The nature of the salt should also be kept in mind, as it can be utilized to modify the physicochemical properties, in particular the solubility, of the active ingredient.

The first active ingredient is preferably micronised using, for example, art known size reduction processes such as mechanical micronisation, jet milling, wet milling, cryogenic milling, ultrasound treatment, high pressure homogenization, microfluidisation and crystallisation processes in order to facilitate its dissolution in the aqueous liquid.

The particle size distribution of the first active ingredient is useful in achieving uniformity within atomized droplets during spray-drying. When assessed by laser diffraction (Sympatec), the $x_{50}$ (median diameter) should be less than 3.0 µm, preferably less than 2.0 µm, or even 1.0 µm. In fact, incorporation of insoluble nanoparticles ($x_{50}$<1000 nm or 200 nm) is contemplated. The $x_{90}$ should be less than 7 μm, preferably less than 5 μm, preferably less than 4 μm or even 3 μm. For nanoparticles, the $x_{90}$ should be less than about 1000 nm.

In preferred embodiments of the dry powder formulation the drug loading for the first active ingredient is suitably less than 30% w/w, preferably less than 10% w/w. At drug contents less than about 30% w/w, the physical properties and aerosol performance of the powder are controlled by the hydrophobic excipient at the interface and the rugous particle morphology, irrespective of whether two or three drugs are incorporated in the particle.

In embodiments, where two or more of the active ingredients are substantially insoluble in water, it may be preferred that they have a similar primary particle size distribution, so that the aerodynamic particle size distribution and pattern of lung deposition are similar for the active ingredients in the mono formulations.

In preferred embodiments, the water solubility of the second active ingredient is greater than 1 mg/ml, preferably greater than 10 mg/ml or 30 mg/ml (See FIG. 2). It should be noted that increasing solids content helps to ensure that the first active ingredient (which is substantially insoluble in water) does not dissolve in the aqueous phase of the feedstock, but it also puts additional restrictions that the solubility of the second active ingredient be high. Achieving the desired physical form for both active ingredients may require a compromise in terms of solids content and drug loading, or even in aerosol performance and blister fill mass. The presence of amorphous active ingredient may also require the addition of an excipient to stabilize the amorphous phase.

In preferred embodiments, the feedstock is comprised of micronised crystals of the first active ingredient dispersed in the continuous phase of an oil-in-water emulsion, and the second active ingredient is dissolved in the continuous phase.

The dispersed oil phase serves as a pore-forming agent to increase particle rugosity in the spray-dried drug product. Suitable pore-forming agents include various fluoriated oils including perflubron, perfluorodecalin, and perfluorooctyl ethane. The emulsion droplets are stabilized by a monolayer of a long-chain phospholipid, which serves as the hydrophobic excipient in the spray-dried particles.

The emulsion may be prepared by first dispersing the hydrophobic excipient in hot distilled water (e.g. 70° C.) using a suitable high shear mechanical mixer (e.g., ULTRA-TURRAX T-25 mixer) at 8000 rpm for 2 to 5 minutes. If the hydrophobic excipient is a phospholipid, a divalent metal e.g. calcium chloride may be added to decrease headgroup hydration as discussed previously. The fluorocarbon is then added drop-wise while mixing. The resulting fluorocarbon-in-water emulsion may then be processed using a high pressure homogenizer to reduce the particle size. Typically, the emulsion is processed for two to five discrete passes at 8,000 to 20,000 psi to produce droplets with a median diameter less than 600 nm. The second active ingredient and other water soluble excipients are dissolved in the continuous phase of the emulsion. The first active ingredient, preferably in micronised form, is added into the continuous phase of the emulsion and mixed and/or homogenized until it has dispersed and a suspension has been formed. On drying, a skin of the hydrophobic phospholipid forms on the surface of the particles. The water soluble drug and glass-forming excipients diffuse throughout the atomized droplets. Eventually, the oil phases evaporates leaving behind pores is the spray-dried particles, and a rugous particle morphology. The crystalline drug, amorphous drug, and phospholipid are substantially phase separated in the spray-dried particles, with the particle surface comprised primarily of the hydrophobic phospholipid excipient. The volume fraction of dispersed phase is generally between 0.03 and 0.5, with values between 0.1 and 0.3 preferred.

In preferred embodiments, the feedstock is aqueous-based, however inhalable medicament powders of the present invention may also be prepared using organic solvents or bisolvent systems. Ethanol/water systems are especially useful as a means to control the solubility of one or more of the materials comprising the particle.

Further, it may be possible formulate two feedstocks (i.e. to disperse the first active ingredient in water and dissolve a hydrophobic excipient and the second active ingredient in ethanol), and then combine the two feedstocks using a twin fluid nozzle, to produce a single feedstock at the point of drying.

It is important to minimize the solubility of the first API to prevent formation of amorphous drug which can have a deleterious effect on long-term stability. The second API is formulated/processed to be amorphous. In this case, it may be advantageous to stabilize the amorphous phase. Excipients which raise $T_g$ (Table 2) are contemplated.

Being a dry powder formulation it is important to control the moisture content of the drug product. For drugs which are not hydrates the moisture content in the powder is preferably less than 5%, more typically less than 3%, or even 2% w/w. The low moisture content is important for maintaining a high glass transition temperature ($\tau_g$) for the amorphous phase comprising the second active ingredient. Moisture content must be high enough, however, to ensure that the powder does not exhibit significant electrostatic attractive forces. The moisture content in the spray-dried powders is determined by Karl Fischer titrimetry.

While the preferred embodiments describe manufacturing processes which utilize aqueous-based feedstocks, the amorphous-coated crystals of the present invention may also be prepared using organic solvents or bisolvent systems.

In one embodiment, micronized crystalline drug A is dispersed in an organic solvent wherein the drug has low solubility, and in which drug B and the hydrophobic excipient are soluble. The resulting feedstock is then spray-dried to produce crystals of drug A coated with an amorphous layer of drug B and hydrophobic excipient. The preferred solvent mixture is ethanol/water. The ratio of ethanol to water may be varied to alter the solubility of the excipient and drugs.

Further, it may be possible formulate two feedstocks (i.e., to disperse a water insoluble drug in water and dissolve a hydrophobic excipient and drug in ethanol), and then combine the two feedstocks in the twin fluid nozzle, to produce a single feedstock at the point of drying.

In the second step of the process of the invention the feedstock prepared in the first step is spray-dried to yield the dry powder formulation of the invention. The resulting spray-dried particles comprise a core of the first active ingredient in substantially crystalline form a second active ingredient in substantially amorphous form, and a pharmaceutically acceptable hydrophobic excipient, wherein the three materials are substantially phase separated in the spray-dried particles.

The spray-drying may be carried out using conventional equipment used to prepare spray dried particles for use in pharmaceuticals that are administered by inhalation. Commercially available spray-dryers include those manufactured by Buchi Ltd. and Niro Corp.

The nature of the particle surface and morphology will be controlled by controlling the solubility and diffusivity of the components within the feedstock. Surface active hydrophobic excipients (e.g., trileucine, phospholipids, fatty acid soaps) may be concentrated at the interface, improving powder fluidization and dispersibility, while also driving increased surface roughness for the particles.

Typically, the feedstock is sprayed into a current of warm filtered air that evaporates the solvent and conveys the dried product to a collector. The spent air is then exhausted with the solvent. Operating conditions of the spray-dryer such as inlet and outlet temperature, feed rate, atomization pressure, flow rate of the drying air, and nozzle configuration can be adjusted in order to produce the required particle size, moisture content, and production yield of the resulting dry particles. The selection of appropriate apparatus and processing conditions are within the purview of a skilled artisan in view of the teachings herein and may be accomplished without undue experimentation. Typical settings are as follows: an air inlet temperature between about 60° C. and about 170° C., such as between 80° C. and 120° C.; an air outlet between about 40° C. to about 120° C., such as about 50° C. and 80° C.; a feed rate between about 3 mL/min to about 15 mL/min; an aspiration air flow of about 300 L/min; and an atomization air flow rate between about 25 L/min and about 50 L/min. The solids content in the spray-drying feedstock will typically be in the range from 0.5% w/w to 20% w/w, such as 1.0% w/w to 10% w/w. The settings will, however, vary depending on the type of equipment used, and the nature of the solvent system employed. In any event, the use of these and similar methods allow formation of particles with diameters appropriate for aerosol deposition into the lung.

In certain embodiments no pore-forming agent is required to achieve the desired powder fluidization and dispersibility. In one such embodiment, crystals of the first active ingredient are dispersed in an aqueous phase containing dissolved hydrophobic excipient and the second active ingredient. In this embodiment, the rugosity of the particle surface is controlled by the content of the poorly soluble hydrophobic excipient, and the spray-drying conditions. For example, the hydrophobic excipient trileucine is surface active, and has limited aqueous solubility. As such, it tends to be present in high concentration at the air/water interface in atomized droplets. During the drying process, the hydrophobic trileucine precipitates before other components in solution, forming a skin of the surface of the atomized droplets. The morphology/rugosity of the coating is then controlled by the rheological properties of the trileucine skin and the drying kinetics. The resulting coating may take on a raisin-like appearance. The rugous layer of hydrophobic trileucine present at the particle interface improves powder fluidization and dispersibility of the resulting medicament particles.

In one embodiment, a phospholipid, such as a long-chain phosphatidylcholine is introduced into the feedstock in the form of liposomes (i.e., there is no dispersed oil phase). The morphology of the resulting particles is controlled by the solubility of the phospholipid and the spray-drying conditions, as discussed above for trileucine.

A pore-forming agent may be added in the first or second step in order to increase the surface rugosity of the particles produced in the third step. This improves the fluidization and dispersibility characteristics of the particles.

The present invention provides a dry powder formulation that comprises the aforementioned spray-dried particles.

The dry powder formulation may comprise 0.1% to 30% w/w of a first active ingredient, 0.1% to 30% of a second active ingredient, and optionally 0.1% to 30% of a third active ingredient.

The particles of the dry powder formulation of the invention suitably have a mass median diameter (MMD) of between 1 and 5 microns, for example of between 1.5 and 4 microns.

The particles of the dry powder formulation of the invention suitably have a mass median aerodynamic diameter (MMAD) of between 1 and 5 microns, for example of between 1 and 3 microns.

The particles of the dry powder formulation of the invention suitably have a rugosity of greater than 1.5, for example from 1.5 to 20, 3 to 15, or 5 to 10.

In order to minimize interpatient variability in lung deposition, the particles of the dry powder formulation of the invention suitably have a fine particle fraction, expressed as a percentage of the nominal dose<3.3 μm (FPF$_{<3.3\ \mu m}$) of greater than 40%, preferably greater than 50%, but especially greater than 60%. Lung deposition as high as 50-60% of the nominal dose (60-80% of the delivered dose) is contemplated.

The fine particle dose of particles of the dry powder formulation of the invention having a diameter less than 4.7 μm (i.e. FPF$_{<4.7\ \mu m}$) is suitably greater than 50%, for example of between 40% and 90%, especially of between 50% and 80%. This minimizes interpatient variability associated with oropharyngeal filtering.

Formulation of both active ingredients components in the same drug particle is useful to ensure that the aerodynamic particle size distribution, and in particular FPF$_{<3.3\ \mu m}$ is consistent for both drugs in a given formulation. As well, the aerodynamic particle size distributions are consistent for the mono-compounds and their combinations.

The differences in FPF$_{<3.3\ \mu m}$ for the two APIs in the engineered particles should be less than 10%, preferably less than 5%, for example less than 1%.

The differences in FPF$_{<3.3\ \mu m}$ for the two APIs in the engineered combination particles relative to the drugs in the corresponding mono-formulations, should be less than 15%, for example less than 10% or less than 5%.

The variability in the fraction of particles of the dry powder formulation of the invention with a $d^2Q$ less than 500 (expressed as the mean variability) is suitably less than 20%, for example less than 10%, especially less than 5% across a range of pressure drops in a dry powder inhaler from 2 kPa to 6 kPa. $d^2Q$ is a measure of inertial impaction.

The mass ratio of active ingredients in the fine particle dose (i.e. the mass ratio of the first active ingredient to the second active ingredient in the nominal dose) is suitably within 10%, preferably within 5%, of the ratio of the nominal doses of the drugs. In the spray-dried particles of the dry powder formulation of the invention the ratio of the two active ingredients is invariant in the fine particle fractions as the active ingredients are co-formulated in a single, particle.

In one embodiment, the present invention provides a dry powder formulation comprising spray-dried particles comprising 0.1% to 30% w/w of a first active ingredient that is substantially insoluble in water, 0.1% to 30% of a water soluble second active ingredient in substantially amorphous form, and a pharmaceutically acceptable hydrophobic excipient, wherein the three materials are substantially phase separated in the spray-dried particles, wherein the particles have a mass median diameter (MMD) of between 1 and 5 microns, a mass median aerodynamic diameter (MMAD) of between 1 and 5 microns, and a rugosity of greater than 1.5. Optionally, a third active ingredient either in crystalline or amorphous form may be formulated into the spray-dried particles. In another embodiment, the present invention provides a dry powder formulation comprising spray-dried particles comprising 0.1% to 30% w/w of indacaterol or a salt thereof, 0.1% to 30% of amorphous glycopyrrolate, and a pharmaceutically acceptable hydrophobic excipient, wherein the particles have a mass median diameter (MMD) of between 1 and 5 microns, a mass median aerodynamic diameter (MMAD) of between 1 and 5 microns, and a rugosity of greater than 1.5.

Various excipients may be included when formulating the medicaments to enhance their stability, biocompatibility or other characteristics. These may include, for example, salts, buffers, chelators, and taste masking agents. The use of these additives will be understood to those of ordinary skill in the art and the specific quantities, ratios, and types of agents can be determined empirically without undue experimentation.

The present invention also provides a unit dosage form, comprising a container containing a dry powder formulation of the present invention.

In one embodiment, the present invention is directed to a unit dosage form, comprising a container containing a dry powder formulation comprising spray-dried particles comprising 0.1% to 30% w/w of a first active ingredient that is in substantially crystalline form, 0.1% to 30% of a second active ingredient in substantially amorphous form, and a pharmaceutically acceptable hydrophobic excipient, wherein the three materials are substantially phase separated in the spray-dried particles, wherein the particles have a mass median diameter (MMD) of between 1 and 5 microns, a mass median aerodynamic diameter (MMAD) of between 1 and 5 microns, and a rugosity of greater than 1.5. Optionally, a third active ingredient either in crystalline or amorphous form may be formulated into the spray-dried particles. In another embodiment, the present invention is directed to a unit dosage form, comprising a container containing a dry powder formulation comprising spray-dried particles comprising 0.1% to 30% w/w of crystalline indacaterol or a salt thereof, 0.1% to 30% of amorphous glycopyrrolate, and a pharmaceutically acceptable hydrophobic excipient, wherein the particles have a mass median diameter (MMD) of between 1 and 10 microns, a mass median aerodynamic diameter (MMAD) of between 1 and 5 microns, and a rugosity of greater than 1.5.

Examples of containers include, but are not limited to, capsules, blisters, or container closure systems made of metal, polymer (e.g., plastic, elastomer), glass, or the like.

The container may be inserted into an aerosolization device. The container may be of a suitable shape, size, and material to contain the dry powder formulation and to provide the dry powder formulation in a usable condition. For example, the capsule or blister may comprise a wall which comprises a material that does not adversely react with the dry powder formulation. In addition, the wall may comprise a material that allows the capsule to be opened to allow the dry powder formulation to be aerosolized. In one or more versions, the wall comprises one or more of gelatin, hydroxypropylmethyl-cellulose (HPMC), polyethyleneglycol-compounded HPMC, hydroxypropylcellulose, agar, aluminium foil, or the like.

The use of foil-foil blisters are particularly preferred given at least the second active ingredient of the dry powder formulation of the present invention are in substantially amorphous form. The selection of appropriate foils for the blister is within the purview of a skilled artisan in view of the teachings herein. The nature of the foils utilized will be driven by the moisture permeability of the seal, and the ability of the material to be formed into a blister of the appropriate size and shape. In one embodiment, the powders are loaded into foil-foil blisters with a fill mass of between 0.5 and 10 mg.

The dry powder formulations of the present invention are useful for treating obstructive or inflammatory airways diseases, especially asthma and chronic obstructive pulmonary disease.

Accordingly the present invention provides a method for the treatment of an obstructive or inflammatory airways disease, especially asthma and chronic obstructive pulmonary disease, which comprises administering to a subject in need thereof an effective amount of the aforementioned dry powder formulation. For example, in one or more embodiments, a subject is administered a dry powder formulation comprising 0.1% to 30% w/w of a first active ingredient in substantially crystalline drug that is coated with a rugous layer comprising 0.1% to 30% of a second active ingredient in substantially amorphous form that is dispersed in a hydrophobic excipient, wherein the particles have a mass median diameter (MMD) of between 1 and 10 microns, a mass median aerodynamic diameter (MMAD) of between 1 and 5 microns, and a rugosity Sv of greater than 1.5.

The present invention also relates to the use of the aforementioned dry powder formulation in the manufacture of a medicament for the treatment of an obstructive or inflammatory airways disease, especially asthma and chronic obstructive pulmonary disease.

The present invention also provides the aforementioned dry powder formulation for use in the treatment of an obstructive or inflammatory airways disease, especially asthma and chronic obstructive pulmonary disease.

Treatment of a disease in accordance with the invention may be symptomatic or prophylactic treatment or both. Obstructive or inflammatory airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other obstructive or inflammatory airways diseases and conditions to which the present invention is applicable include acute/adult respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further obstructive or inflammatory airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

The dry powder formulation of the present invention is especially useful for treating asthma and COPD.

The present invention also provides a delivery system, comprising an inhaler and a dry powder formulation of the invention.

In one embodiment, the present invention is directed to a delivery system, comprising an inhaler and a dry powder formulation for inhalation comprising spray-dried particles that comprise a core of a first active ingredient in substantially crystalline form, a second active ingredient in substantially amorphous form, and a pharmaceutically acceptable hydrophobic excipient. The first active ingredient, second active ingredient and hydrophobic excipient are substantially phase separated in the spray-dried particles.

In a preferred embodiment, particles comprising 0.1% to 30% w/w of a first active ingredient that is in substantially crystalline form, 0.1% to 30% of a second active ingredient in substantially amorphous form, and a pharmaceutically acceptable hydrophobic excipient, wherein the particles have a mass median diameter (MMD) of between 1 and 5 microns, a mass median aerodynamic diameter (MMAD) of between 1 and 5 microns, and a rugosity of greater than 1.5.

In another embodiment, the present invention is directed to a delivery system, comprising an inhaler and a dry powder formulation comprising spray-dried particles comprising 0.1% to 30% w/w of a first active ingredient that is in substantially crystalline form, 0.1% to 30% of a second active ingredient in substantially amorphous form, and a pharmaceutically acceptable hydrophobic excipient, wherein the particles have a mass median diameter (MMD) of between 1 and 5 microns, a mass median aerodynamic diameter (MMAD) of between 1 and 5 microns, and a rugosity of greater than 1.5.

In yet another embodiment, the present invention is directed to a delivery system, comprising an inhaler and a dry powder formulation comprising spray-dried particles comprising 0.1% to 30% w/w of crystalline indacaterol or a salt thereof, 0.1% to 30% of amorphous glycopyrrolate, and a pharmaceutically acceptable hydrophobic excipient, wherein the particles have a mass median diameter (MMD) of between 1 and 5 microns, a mass median aerodynamic diameter (MMAD) of between 1 and 5 microns, and a rugosity of greater than 1.5. [QVA149]

Suitable inhalers include dry powder inhaler (DPIs). Some such inhalers include those where the dry powder is stored in a capsule and the patient loads one or more of the capsules into the device prior to use. Other dry powder inhalers include those that are loaded with a magazine of capsules. Other dry powder inhalers include those that are loaded with a blister pack comprising several doses of powder. Given the amorphous nature of at least one of the active ingredients of the inhalable medicament particles of the present it is preferable for the medicament containing such particles to be pre-packaged in foil-foil blisters, for example in a cartridge, strip or wheel.

Preferred dry powder inhalers include multidose dry powder inhalers such as the DISKUS™ (GSK, described in U.S. Pat. No. 6,536,427), DISKHALER™ (GSK, described in WO 97/25086), GEMINI™ (GSK, described in WO 05/14089), GYROHALER™ (Vectura, described in WO 05/37353), PROHALER™ (Valois, described in WO 03/77979) and TWISTHALER™ (Merck, described in WO 93/00123, WO 94/14492 and WO 97/30743) inhalers.

Preferred single dose dry powder inhalers include the AEROLIZER™ (Novartis, described in U.S. Pat. No. 3,991,761) and BREEZHALER™ (Novartis, described in WO 05/113042) inhalers. These tend to be less complicated to operate than many multidose dry powder inhalers.

Preferred single dose blister inhalers, which some patient find easier and more convenient to use to deliver medicaments requiring once daily administration, include the inhaler described by Nektar Therapeutics in WO 08/51621 and WO 09/117,112.

Reservoir-based dry powder inhalers are generally not preferred for the powders of the invention, due to potential stability issues associated with the amorphous active ingredient(s).

Single dose capsule dry powder inhalers are generally not preferred for asthma patients, or when capsule handling is difficult or the total powder masses to be delivered (typically 1 to 2 mg) are lower than is typically required for such inhalers.

Particularly preferred inhalers are multidose dry powder inhalers where the energy for fluidizing and dispersing the powder is supplied by the patient (i.e. "passive" MD-DPIs). The powders of the present invention fluidize and disperse effectively at low peak inspiratory flow rates (PIF). As a result, the small changes in powder dispersion with PIF observed effectively balance the increases in inertial impaction which occur with increases in PIF, leading to flow rate independent lung deposition. The absence of flow rate dependence observed for powders of the present invention, drives reductions in overall interpatient variability. Suitable blister-based passive multidose inhalers include the DISKUS™ (GSK), GYROHALER™ (Vectura), DISKHALER™ (GSK), GEMINI™ (GSK), and PROHALER™ (Valois) devices.

Some patients may prefer to use an "active" multidose dry powder inhaler where the energy for fluidizing and dispersing the powder is supplied by the inhaler. Suitable such inhalers include pressurizable dry powder inhalers, as disclosed, for example in WO 96/09085, WO00/072904, WO00/021594 and WO 01/043530, and ASPIRAIR™ (Vectura) inhalers. Other active devices may include those available from MicroDose Technologies Inc., such as the device described in United States patent publication no. 20050183724. Preferred devices would be those which not only disperse the powders uniformly with an active component of the device (e.g., compressed air, impeller), but also standardize the breathing profile so as to create reverse flow rate dependence (i.e., increases in lung deposition with decreases in PIFR), that is common with active DPIs.

Additional embodiments and features are set forth in part in the description that follows, and in part will become apparent to those skilled in the art upon examination of the specification or may be learned by the practice of the invention.

This invention is further illustrated by the following examples which should not be construed as limiting.

EXAMPLES

Example 1

Preparation of a Dry Powder Formulation Comprising Spray-Dried Particles that Contain Formoterol and Budesonide A dry powder formulation comprising spray-dried particles that contain formoterol fumarate and budesonide were prepared by a two-step manufacturing process.

In the first step, 1.38 g of distearoylphosphatidylcholine (DSPC) (Genzyme Pharmaceuticals, Cambridge, Mass., USA), and 119.6 mg calcium chloride (J T Baker) were dispersed in 164 g of hot deionised water (T=70° C.) using an ULTRA-TURRAX™ high shear mixer (model T-25) at 10,000 rpm for about 1 minute. The resulting DSPC/$CaCl_2$ dispersion was then cooled in an ice bath. 98 mg of micronised formoterol fumarate (Industriele Chimica s.r.i, Italy) was added while mixing. The formoterol has a water solubility of about 1 mg/ml, and as such, dissolves in the aqueous phase. The resulting formoterol/DSPC/$CaCl_2$ dispersion was then passed through a high pressure homogenizer (AVESTIN EMULSIFLEX-C5™ high pressure homogenizer, Ottawa, Canada) at 20,000 pounds per square inch (psi) for 2 passes. 1.45 g of micronised crystalline budesonide (Industriale Chimica s.r.i, Italy) was dispersed in the aqueous phase and the resulting dispersion was passed through the high pressure homogenizer at 20,000 psi for an additional 3 passes.

In the second step, the resulting feedstock was spray-dried on a BUCHI B-191™ mini spray-dryer (Büchi, Flawil, Switzerland). The composition of the dry components of the feedstock is listed in Table 3 below. The following spray conditions were employed: total flow rate=28 SCFM, inlet temperature=85° C., outlet temperature=57° C., feed pump=~2 mL $min^{-1}$, atomizer pressure=60 psig, atomizer flow rate=34 cm (rotameter).

TABLE 3

Composition of spray-dried particles comprising formoterol fumarate and budesonide spray-dried in a single particle

| Component | Composition |
|---|---|
| Distearoylphosphatidylcholine (DSPC) | 44.7% |
| Calcium Chloride ($CaCl_2$) | 3.8% |
| Formoterol fumarate | 3.1% |
| Budesonide | 48.4% |

A free flowing white powder was collected using a cyclone separator. The geometric diameter of the engineered particles was measured using laser diffraction (SYMPATEC HELOS™ H1006, Clausthal-Zellerfeld, Germany), where a volume weighted mean diameter (VMD) of 2.1 μm was found. Scanning electron microscopy (SEM) analysis showed the powders to be small wrinkled particles with high surface roughness. There was no evidence of any unincorporated budesonide drug crystals in the five SEM views provided for each collector. The composite particles contain micronised crystalline budesonide crystals coated with an amorphous layer of formoterol fumarate and DSPC/$CaCl_2$. No pore-forming agent was used in the manufacture of this powder.

Example 2

Preparation of Dry Powder Formulations Comprising Spray-Dried Particles that Contain Fixed Dose Combinations of Micronised Indacaterol Maleate Crystals Coated with Amorphous Glycopyrrolate and Phospholipid In this Example inhalable dry powders comprising indacaterol maleate, glycopyrrolate, and excipients (distearoylphosphatidylcholine (DSPC), calcium chloride, and trehalose) were manufactured by spray drying an emulsion-based feedstock.

The feedstock was prepared by mixing an individually prepared vehicle emulsion and a drug annex solution.

The vehicle emulsion was prepared by emulsifying perfluorooctyl bromide (PFOB, perflubron) in an aqueous dispersion of DSPC containing dissolved $CaCl_2$. A two-step process was employed in which a coarse emulsion was prepared with a ULTRA-TURRAX™ high shear mixer, followed by homogenization through an AVESTIN C50™ homogenizer. The resultant vehicle emulsion was a stable oil-in-water emulsion with a median emulsion droplet size in the range of 0.20-0.40 µm.

The drug annex solution was prepared by suspending micronised crystals of indacaterol maleate in water using a ULTRA-TURRAX™ high shear mixer, then dissolving glycopyrrolate in the aqueous medium. In those emulsions where trehalose was used as a glass forming agent, the weight ratio of trehalose to glycopyrrolate was 2:1 w/w.

The feedstock was prepared by mixing appropriate proportions of the vehicle emulsion and the drug annex solution to obtain a solution with a solids content of 3% w/v, and a PFOB volume fraction of about 0.2. Thus, the final feedstock consisted of an aqueous solution (continuous phase) of glycopyrrolate, trehalose, and calcium chloride, with two discrete phases: micronised indacaterol maleate crystals and emulsion droplets stabilized with DSPC.

The spray dryer configuration consisted of a single, twin-fluid atomizer, a drying chamber, a cyclone, an adaptor, an isolation valve, and a 1 L collector in a temperature-controlled jacket. The spray drying parameters used for manufacturing the inhalable medicament powders are shown in Table 4:

TABLE 4

Spray drying parameters used to prepare dry powder formulations comprising spray-dried particles comprising fixed dose combinations of indacaterol maleate and glycopyrrolate

| Process Parameters | Value |
| --- | --- |
| Solid Concentration (% w/v) | 3.0 |
| Inlet temperature/° C. | 97 ± 3 |
| Outlet temperature/° C. | 60 ± 3 |
| Collector temperature/° C. | 60 ± 3 |
| Drying air flow rate/L/min | 600 ± 10 |
| Atomizer flow rate/L/Min | 25 ± 2 |
| Liquid feed rate/mL/min | 10.0 ± 0.5 |

During spray drying, a peristaltic pump fed the feedstock fluid into the atomizer, generating a fine spray of liquid droplets. Pre-heated drying air was fed into drying chamber, and mixed with the droplets, resulting in the formation of solid particles comprising micronised indacaterol maleate crystals coated with a rugous layer of amorphous glycopyrrolate and DSPC. The particles were collected with a yield of approximately 60% using a cyclone separator. The nominal compositions of the spray-dried powders are presented in Table 5.

TABLE 5

Composition of spray-dried particles comprising fixed dose combinations of indacaterol maleate and glycopyrrolate

| Component | Nominal content (% w/w) | | | | |
| --- | --- | --- | --- | --- | --- |
| | Lot A1 | Lot A2 | Lot A3 | Lot A4 | Lot A5 |
| indacaterol maleate[1] | 7.8 | 7.8 | 7.8 | 7.8 | 7.8 |
| glycopyrrolate[2] | 1.3 | 2.5 | 2.5 | 2.5 | 2.5 |
| trehalose | — | — | 5.0 | — | 5.0 |
| DSPC[3] | 84.9 | 83.8 | 79.1 | 83.8 | 79.1 |
| calcium chloride dihydrate | 6.0 | 5.9 | 5.6 | 5.9 | 5.6 |
| pH[4] | — | — | — | 5.0 | 5.0 | where
[1]Represents 6.0% w/w indacaterol
[2]Represents 1.0% or 2.0% w/w glycopyrrolate
[3]The ratio of DSPC:$CaCl_2$ was 2:1 mol:mol
[4]The pH was adjusted to pH 5.0 with NaOH Example 3

Physicochemical Properties of a Dry Powder Formulation Comprising Spray-Dried Particles that Contain Fixed Dose Combinations of Indacaterol Maleate and Glycopyrrolate In this Example the physicochemical properties (e.g. morphology, primary particle size) of the powders prepared according to Example 2 were measured.

Scanning electron microscopy (SEM) was used to qualitatively assess the morphology of the spray-dried particles. Samples were mounted on silicon wafers that were then mounted on top of double-sided carbon tape on an aluminium SEM stub. The mounted powders were then sputter-coated with gold:palladium in a DENTON™ sputter-coater for 60 to 90 seconds at 75 mTorr and 42 mA, producing a coating thickness of about 150 Å. Images were taken with a PHILIPS™ XL30 ESEM™ scanning electron microscope operated in high vacuum mode using an Everhart-Thornley detector to capture secondary electrons for the image composition. The accelerating voltage was set at 20 kV using a $LaB_6$ source. The working distance was between 5 and 6 mm.

The SEM images of indacaterol/glycopyrrolate powders (lots A2, A3, A4, A5) show evidence of significant porosity, a characteristic of the emulsion-based spray-drying process. A qualitative assessment suggests that particles formulated with trehalose are larger under the drying conditions employed.

Primary particle size distributions were determined using laser diffraction. Powder samples were measured using a SYMPATEC HELOS particle size analyser equipped with an ASPIROS micro dose feeder and a RODOS dry powder dispersing unit (Sympatec GmbH, Clausthal-Zellerfeld, Germany). The following settings were applied for analysis of samples: a sample mass of approximately 10 mg, a triggering optical concentration ($C_{opt}$) of approximately 1%, and a driving pressure of 4 bar. Data were collected over a measurement duration of 10 seconds. Particle size distributions were calculated by the instrument software using the Fraunhofer model. Prior to measurement of sample$_s$, the system suitability was assessed by measurement of the primary particle size distribution of a silicon carbide reference standard supplied by Sympatec GmbH.

The MMD (x50) of the trehalose-based powders (2.8 µm) were about 1 µm larger than those of the powders prepared without trehalose (1.7 to 1.8 µm).

Example 4

Aerosol Performance of Dry Powder Inhaler Formulations Comprising Spray-Dried Particles that Contain Fixed Dose Combinations of Indacaterol Maleate and Glycopyrrolate Delivered by a Passive Dry Powder Inhaler The lung delivery performance of representative dry powder formulations comprising spray-dried particles that contain fixed dose combinations of indacaterol maleate and glycopyrrolate prepared according to Example 2 were characterized by filling the powder into a foil-foil blister, and dispersing the powder with a dry powder inhaler described in international patent application WO 08/51621 i.e. a portable, passive, unit dose blister based dry powder inhaler being developed by Novartis (San Carlos, Calif., USA).

The aerodynamic particle size distribution (aPSD) of the resulting aerosol dose was assessed using a NEXT GENERATION IMPACTOR™ at flow rates of 35 LPM and 47 LPM, corresponding to inhaler pressure drops of 4 kPa and 6 kPa, respectively. Note for present purposes flow rate and pressure drop are related via the inhaler flow resistance, and are used interchangeably. The mass distribution of each active ingredient on the cascade impactor stages was determined using an HPLC assay.

Aerosol metrics determined for a representative powder formulation (Lot A2) having a theoretical bulk powder composition of 6% indacaterol (7.8% maleate salt), 2% glycopyrrolate (2.5%), 83.8% DSPC, and 5.9% $CaCl_2$ are presented in Table 6.

TABLE 6

Aerosol metrics for a dry powder formulation containing spray-dried particles comprising indacaterol maleate and glycopyrrolate delivered with a passive dry powder inhaler

| Pressure Drop (kPa) | Flow Rate (L/min) | Aerosol Metric | Indacaterol maleate | Glycopyrrolate |
|---|---|---|---|---|
| 4 | 35 | MMAD (µm) | 2.8 | 2.7 |
|   |    | $FPF_{<3.3\,\mu m}$ (% DD) | 57 | 57 |
|   |    | $d^2Q < 500$ | 65 | 62 |
| 6 | 47 | MMAD (µm) | 2.3 | 2.2 |
|   |    | $FPF_{<3.3\,\mu m}$ (% DD) | 69 | 68 |
|   |    | $d^2Q < 500$ | 68 | 67 |

Table 6 presents the mass median aerodynamic diameter (MMAD) and the $FPF_{<3.3\,\mu m}$ for each drug component at two distinct flow rates, roughly corresponding to comfortable and forceful inhalation manoeuvres. At a given flow rate, the MMAD and $FPF_{<3.3\,\mu m}$ values are largely equivalent (variation less than 2%). This provides confirmation that the two drug substances have been effectively formulated in a single particle.

This is distinct from fixed dose combinations comprising micronised drug blends, where significant differences in the fine particle dose are often observed for each active ingredient as a result of different adhesive properties with the coarse lactose carrier particles.

The formulations of the present invention are expected to lead to significant improvements in lung targeting and dose consistency relative to current marketed inhalers based on blends or agglomerates of micronized drug.

In terms of lung targeting, the best correlate of total lung deposition has been found to be the fraction of particles less than about 3 µm. Based on this metric, it is anticipated that total lung deposition will be approximately 60% of the delivered dose. The improved lung targeting lowers the required nominal dose, while significantly reducing oropharyngeal deposition. This is expected to reduce the potential for opportunistic infections (e.g., candidiasis or pneumonia) in asthma/COPD patients which result from use of corticosteroids. The improved targeting may also lead to reduced systemic drug concentrations when the therapeutic is orally bioavailable (e.g., indacaterol).

In terms of improved dose consistency, the spray-dried powders of the present invention are expected to improve dose consistency by one or more of: (a) reducing the variability associated with oropharyngeal filtering; (b) reducing the variability associated with patient breathing manoeuvres, in particular variations with peak inspiratory flow rate; (c) reductions in variability in fixed dose combinations associated with differences in adhesive properties of the two drugs with the carrier.

Total lung deposition as a function of variations in flow rate (Q) is dependent not only on the aerodynamic particle size distribution of the aerosol, but also on the variations in inertial impaction which occur with changes in flow rate. In other words, for a given aPSD, the lung dose is expected to decrease as the flow rate increases. In order to achieve flow rate independence in-vivo, it is important to achieve a balance of these two opposing factors. A simple way to account for the dependence of lung dose on both variables, i.e. aerodynamic particle size cutoff diameter, d, and flow rate, Q, is to express the aPSD in terms of a fine particle fraction cut-off which incorporates both variables. Assuming oropharyngeal losses are determined largely by inertial impaction, the cut-off for lung dose may be expressed in terms of the impaction parameter, $d^2Q$. The selected cut-off $d^2Q$ of 500 µm²·L/min was chosen to represent a range of inhalers, based on the fact that the best correlate of lung deposition is found for the fraction of particles with an aerodynamic size of less than 3 µm, and a medium resistance inhaler is typically tested at a flow rate of about 60 L/min.

The % deviation in $FPF_{d2Q<500}$ in going from 35 L/min to 47 L/min was 4.6% for indacaterol, and 8.1% for glycopyrrolate. Hence, formulation as an engineered powder dramatically reduces the observed flow rate dependence in the anticipated lung dose, where for example the total lung deposition for budesonide from the PULMICORT™ TURBUHALER™ decreases from 28% to 15% in going from a forceful to comfortable inhalation manoeuvre. This is consistent with what has been observed clinically for monotherapies with engineered particles (see Duddu et al: Improved lung delivery from a passive dry powder inhaler using an engineered PulmoSphere™ powder. *Pharm Res.* 2002, 19:689-695).

The high fine particle fractions observed are expected to lead to lung deliveries in patients of >60% of the delivered dose. This in turn is expected to reduce the in-vivo variability in the lung dose to ca., 10-20%. This is compared to 30-50% for standard micronized drug blends (see Olsson B, Borgstrom L: Oropharyngeal deposition of drug aerosols from inhalation products. *Respiratory Drug Delivery* 2006, pp. 175-182).

Formulation of the two actives in a single engineered particle practically eliminates variability associated with the differences in adhesive properties between drug and carrier. This enables effective delivery of the two active ingredients to different targets on the same cell.

Example 5

An X-Ray Powder Diffraction Study of Dry Powder Formulations Comprising Spray-Dried Particles Comprising Micronised Indacaterol Maleate Crystals Coated with a Porous Layer of Amorphous Glycopyrrolate and Phospholipid Spray-dried particles comprising fixed dose combinations of indacaterol maleate and glycopyrrolate were prepared using the process described in Example 2 (Table 7). The ratio of indacaterol maleate to glycopyrrolate was 3:1 in both formulations. The concentration of each active ingredient is expressed on a free-base basis. A vehicle formulation (lot V1), was also prepared. This formulation contains a 2:1 mol:mol ratio of DSPC:$CaCl_2$.

TABLE 7

Composition of spray-dried particles comprising fixed dose combinations of indacaterol maleate and glycopyrrolate utilized in XRPD studies

| | indacaterol (% w/w) | glycopyrrolate (% w/w) | DSPC:$CaCl_2$ (% w/w) | % solids (w/v) |
|---|---|---|---|---|
| Lot A2 | 6 | 2 | 90.2 | 3 |
| Lot B1 | 45 | 15 | 26.7 | 3 |
| Lot V1 | 0 | 0 | 100 | 3 |

The X-ray powder diffraction (XRPD) patterns of the test powders (see FIG. 3) were measured using a SHIMADZU XRD-6000™ X-ray powder diffraction system with a graphite monochromator and scintillation detector (Shimadzu Corporation, Japan). Samples were scanned from 3° to 40° 2θ, at 0.4° 2θ/minute, with a step size of 0.02° 2θ, using a Cu radiation source with a wavelength of 1.54 Å operated at 40 kV and 40 mA. In this work, 0.5° divergent, 0.5° scattering, and 0.3 mm receiving slits were used. One sample of each material was prepared by packing bulk powder into a chromium-plated copper sample holder, and a single measurement was obtained from that sample. The environmental chamber on the X-ray instrument was purged with dry $N_2$ gas during data acquisition.

Figure 3:
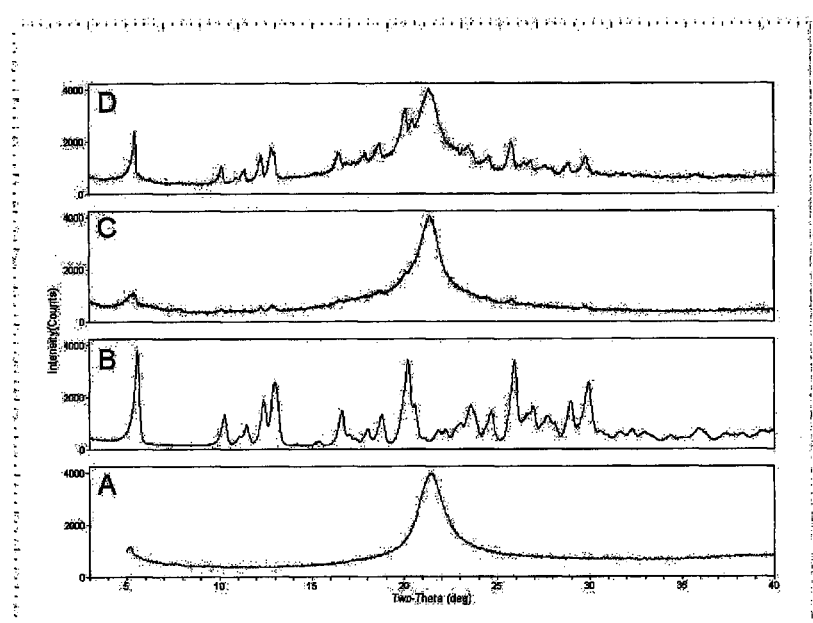

FIG. 3 shows the wide-angle X-ray powder diffraction patterns of the two fixed-dose combination formulations of indacaterol and glycopyrrolate. The X-ray powder diffraction patterns of (highly crystalline) indacaterol raw material and a placebo formulation (DSPC:$CaCl_2$) are provided for comparison. Both fixed-dose combination powders exhibit diffraction peaks that are indicative of the presence of crystalline indacaterol, as shown by the agreement of the peak positions of the formulations with those in the powder pattern of indacaterol API. The powder pattern of each formulation also has a broad, conspicuous peak at 21.3° 2θ, which arises from DSPC. Besides this peak, all other peaks can be assigned to indacaterol, indicating that the glycopyrrolate is amorphous. Thus, the powder patterns of both formulations indicate that the two drugs are present in separate phases, wherein indacaterol is crystalline and glycopyrrolate is amorphous. As well, the DSPC is present as a gel phase with its characteristic diffraction peak. Hence, the two drugs and the hydrophobic excipient are effectively phase separated into their own domains within the spray-dried particles.

Example 6

Effect of Added Glass Stabilizing Excipient on the Chemical Stability of Dry Powder Formulations Comprising Crystalline Indacaterol Maleate, Amorphous Glycopyrrolate, and a Hydrophobic Excipient (DSPC or Leucine)

A number of formulations comprising fixed dose combinations of indacaterol maleate and glycopyrrolate are presented in Table 8. There are two principal groups of formulations. The first group of formulations utilizes DSPC as the hydrophobic excipient and an emulsion-based feedstock. The second group utilizes leucine as the hydrophobic excipient with no emulsion phase The emulsion-based formulations are prepared by spray-drying a base feedstock comprising dispersed indacaterol maleate crystals in a submicron PFOB-in-water emulsion, in which the emulsion droplets are stabilized by a 2:1 mol:mol ratio of DSPC:$CaCl_2$. Glycopyrrolate is dissolved in the continuous phase of the emulsion, and is present as an amorphous solid in the spray-dried particles. Formulation C3 adds 20 mM sodium maleate (pH 5.7) buffer to the base DSPC formulation. Increases in pH decrease indacaterol solubility, thereby limiting amorphous forms of indacaterol. Sodium maleate also serves as a glass stabilizing agent, improving the physical and chemical stability of the amorphous phase. Formulation C4 contains added trehalose, an alternative glass stabilizing excipient. Formulation C5 contains trehalose and pH adjustment. Formulation C6 explores fixed dose combinations comprising higher glycopyrrolate concentrations. Formulations C9 and C10 are leucine-based formulations containing trisodium citrate and trehalose as glass stabilizing agents, respectively. The DSPC-containing formulations were prepared by first creating a submicron perflubron-in-water emulsion with an AVESTIN C50™ homogenizer. The volume fraction of perflubron in the emulsion was 0.12 v/v. Glycopyrrolate and excipients are dissolved in the continuous phase of the emulsion and micronized indacaterol maleate is dispersed in the continuous phase of the emulsion. The total solids content was 5% w/v. The leucine-based feedstocks are prepared by dissolving the excipients and glycopyrrolate in water. Micronized indacaterol is then added to the chilled solution and dispersed with an ULTRA TURRAX™ high shear mixer. The feedstock to be spray-dried contained a solids content of 2.0% w/v. The formulations were spray-dried on a laboratory-scale spray-drier. The spray-drier hardware consists of a twin fluid atomizer, drying chamber, a cyclone, and a 1 L collector in a temperature controlled jacket. The target spray-drying conditions were: inlet temperature=97±3° C., outlet temperature=60±3° C., collector temperature=60±3° C., drying airflow rate=600±10 L/min, atomizer airflow rate=25±2 L/min, liquid feed rate=10.0±0.5 mL/min. These spray-dry conditions produce spray-dried particles with a target tap density of about 0.05 g/mL.

TABLE 8

Compositions of fixed dose combinations comprising indacaterol maleate and glycopyrrolate

| Lot # | Indacaterol (% w/w) | Glycopyrrolate (% w/w) | 2:1 mol:mol DSPC:CaCl$_2$ | Trehalose (% w/w) | Trisodium citrate (% w/w) | Leucine (% w/w) | pH |
|---|---|---|---|---|---|---|---|
| C1 | 0 | 3.6 | Balance | 0 | 0 | 0 | — |
| C2 | 6 | 3.6 | Balance | 0 | 0 | 0 | — |
| C3 | 6 | 3.6 | Balance | 0 | 0 | 0 | 5.7 |
| C4 | 6 | 3.6 | Balance | 10 | 0 | 0 | — |
| C5 | 6 | 3.6 | Balance | 10 | 0 | 0 | 5.7 |
| C6 | 6 | 5 | Balance | 10 | 0 | 0 | — |
| C9 | 6 | 3.6 | 0 | 0 | 10 | Balance | 5.7 |
| C10 | 6 | 3.6 | 0 | 10 | 0 | Balance | — |

The presence of dissolved indacaterol results in amorphous indacaterol in the spray-dried drug product. Amorphous indacaterol is less stable chemically, with increases in hydrolysis and enantiomer formation on storage. The presence of amorphous glycopyrrolate may also enhance degradation, as amorphous glycopyrrolate may plasticize the amorphous indacaterol material. The spray-dried formulations comprising indacaterol can be effectively stabilized against chemical degradation by minimizing the dissolved fraction via process changes (e.g., decreasing the temperature of the feedstock, increasing the solids content in the feedstock, or spray-blending of particles with a higher indacaterol content with particles comprising excipients only. Alternatively, the amorphous phase may be stabilized by the addition of a glass stabilizing excipient.

The chemical stability of the formulations in Table 8 were assessed by reverse phase HPLC. The presence of a glass stabilizing excipient (e.g., trehalose, sodium maleate, trisodium citrate) was necessary to effectively stabilize the amorphous phase within the spray-dried indacaterol/glycopyrrolate particles. After 3 months storage of bulk powder packaged in a laminated foil pouch at 40° C./75% relative humidity (RH), there was only minimal chemical degradation noted for the formulations containing sodium maleate. Total indacaterol enantiomer content for C3 and C5 remained below 0.5%, while total indacaterol hydrolysis products remained below 0.1%. In these same formulations, no glycopyrrolate degradation was observed over 3 months at 40° C./75% RH. In contrast formulation C2 with no added glass-forming agent, had an enantiomer content greater than 3% and total hydrolysis greater than 0.4% after 3 months at 40° C./75% RH. Limited chemical degradation was also observed for the leucine-based formulations (e.g., C10), where indacaterol enantiomer content remained less than 0.75%, and total hydrolysis products less than 0.4%. No physical changes in the spray-dried particles are noted on storage.

Hence, it has been surprisingly found that it is possible to engineer spray-dried particles in which there are three separate phases (domains) which remain physically and chemically stable on storage. These include seemingly incompatible crystalline and amorphous phases of two distinct drug substances, and a gel phase of a hydrophobic excipient.

Example 7

Preparation of a Fixed Dose Combination Comprising Indacaterol Maleate, Mometasone Furoate, and Glycopyrrolate The composition of a fixed dose combination product comprising indacaterol maleate, mometasone furoate, and glycopyrrolate is detailed in Table 9.

TABLE 9

Composition of spray-dried powder comprising a fixed dose combination comprising a long-acting beta-agonist, a long-acting anti-muscarinic, and a corticosteroid

| Component | Percentage in Spray-Dried Particle |
|---|---|
| Indacaterol maleate | 7.8 |
| Mometasone furoate | 4.0 |
| Glycopyrrolate | 5.0 |
| Maleic acid | 4.8 |
| Sodium hydroxide | 2.1 |
| DSPC | 71.3 |
| Calcium chloride | 5.0 |

The spray-dried powder is prepared by the emulsion-based spray-drying process described previously in Example 2. Indacaterol maleate and mometasone furoate are dispersed as micronized crystals in the continuous phase of a submicron perflubron-in-water emulsion. Glycopyrrolate is dissolved in the continuous phase of the emulsion. The continuous phase is comprised of 20 mM sodium maleate buffer (pH 5.5) prepared from maleic acid and sodium hydroxide. The emulsion feedstock has a dispersed phase volume fraction of 0.18. The droplets are stabilized by a monolayer of distearoylphosphatidyl-choline (DSPC) and calcium chloride. The ratio of DSPC:calcium chloride is 2:1 mol:mol. The total solids content in the feedstock is 4.0%.

The complex emulsion-based feedstock comprising submicron emulsion droplets, two dispersed APIs, one dissolved API, and a buffer (glass stabilizing agent) is spray-dried on a portable spray-drying system according to the process conditions described in Table 4. The resulting powder is comprised of particles comprising crystalline indacaterol and mometasone coated with amorphous glycopyrrolate and DSPC/CaCl$_2$. The physico-chemical and aerosol properties of the spray-dried powder are controlled by hollow and porous particle morphology and the low surface energy afforded by the hydrophobic DSPC excipient which is concentrated at the particle interface.

The various features and embodiments of the present invention, referred to in individual sections above apply, as appropriate, to other sections, mutatis mutandis. Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A dry powder formulation for inhalation comprising spray-dried particles that comprise a core of a first active ingredient in substantially crystalline form that is coated with a layer of a second active ingredient in substantially amorphous form that is dispersed in a pharmaceutically acceptable hydrophobic excipient.

2. A formulation according to claim 1, wherein the active ingredients are selected from bronchodilators, anti-inflammatories, antihistamines, decongestants and anti-tussive drug substances.

3. A formulation according to claim 2, wherein the first active ingredient is a β2-agonist and the second active ingredient is a steroid.

4. A formulation according to claim 2, wherein the first active ingredient is a β2-agonist and the second active ingredient is an anti-muscarinic antagonist.

5. A formulation according to claim 1, wherein the first active ingredient is a β2-agonist, the second active ingredient is an anti-muscarinic antagonist, and the formulation also contains a third active ingredient, which is a steroid.

6. A formulation according to claim 1 that further comprises a third active ingredient that is substantially amorphous and is dispersed in the hydrophobic excipient.

7. A formulation according to claim 6 wherein the active ingredients are indacaterol or a salt thereof, mometasone furoate and glycopyrrolate.

8. A formulation according to claim 1, wherein the hydrophobic excipient is a phospholipid.

9. A formulation according to claim 1 in powdered form wherein the inhalable medicament particles comprise 0.1% to 30% w/w of a first active ingredient in substantially crystalline drug that is coated with a rugous layer comprising 0.1% to 30% of a second active ingredient in substantially amorphous form that is dispersed in a hydrophobic excipient, wherein the particles have a mass median diameter (MMD) of between 1 and 10 microns, a mass median aerodynamic diameter (MMAD) of between 1 and 5 microns, and a rugosity Sv of greater than 1.5.

10. A formulation according to claim 9, wherein the fine particle dose less than 3.3 μm is greater than 40% to minimize interpatient variability associated with oropharyngeal deposition.

11. A formulation according to claim 9, wherein variability in the fraction of particles with a d2Q <500 (expressed as the mean variability) is less than 20% across a range of pressure drops in a dry powder inhaler from 2 kPa to 6 kPa.

12. A formulation according to claim 9, wherein the mass ratio of first active ingredient or the second active ingredient or any optional third active ingredient in the fine particle dose is within 10% of the ratio of the nominal doses of the drugs.

13. A delivery system, comprising an inhaler and a dry powder formulation for inhalation according to claim 1.

* * * * *